(12) United States Patent
Hefner, Jr.

(10) Patent No.: US 9,284,434 B2
(45) Date of Patent: Mar. 15, 2016

(54) EPOXY RESIN COMPOSITIONS

(75) Inventor: Robert E. Hefner, Jr., Rosharon, TX (US)

(73) Assignee: BLUE CUBE IP LLC, Midland, MI (US)

( * ) Notice: Subject to any disclaimer, the term of this patent is extended or adjusted under 35 U.S.C. 154(b) by 204 days.

(21) Appl. No.: 13/816,777

(22) PCT Filed: Sep. 7, 2011

(86) PCT No.: PCT/US2011/050613
§ 371 (c)(1),
(2), (4) Date: Feb. 13, 2013

(87) PCT Pub. No.: WO2012/044443
PCT Pub. Date: Apr. 5, 2012

(65) Prior Publication Data
US 2014/0194554 A1    Jul. 10, 2014

Related U.S. Application Data

(60) Provisional application No. 61/388,064, filed on Sep. 30, 2010.

(51) Int. Cl.
| | |
|---|---|
| C08G 59/14 | (2006.01) |
| C09D 163/00 | (2006.01) |
| C09J 163/00 | (2006.01) |
| C08K 5/01 | (2006.01) |
| C08G 59/06 | (2006.01) |
| C08L 63/00 | (2006.01) |
| C07K 16/46 | (2006.01) |
| B32B 27/38 | (2006.01) |

(52) U.S. Cl.
CPC .................. *C08K 5/01* (2013.01); *C07K 16/468* (2013.01); *C08G 59/066* (2013.01); *C08G 59/145* (2013.01); *C08L 63/00* (2013.01); *C09D 163/00* (2013.01); *C09J 163/00* (2013.01)

(58) Field of Classification Search
None
See application file for complete search history.

(56) References Cited

U.S. PATENT DOCUMENTS

| | | | |
|---|---|---|---|
| 3,256,226 A | 6/1966 | Fekete et al. | |
| 3,271,363 A | 9/1966 | Nikles et al. | |
| 3,639,655 A | 2/1972 | Jones | |
| 3,864,316 A | 2/1975 | Robinson | |
| 4,125,558 A | 11/1978 | Torsi | |
| 4,284,574 A | 8/1981 | Bagga | |
| 4,373,073 A | 2/1983 | Wojtech et al. | |
| 4,417,033 A | 11/1983 | Bowditch | |
| 4,544,731 A | 10/1985 | Cavitt et al. | |
| 5,128,491 A | 7/1992 | Cheng | |
| 5,780,582 A | 7/1998 | Wang et al. | |
| 5,959,061 A | 9/1999 | Neumann et al. | |
| 6,211,389 B1 | 4/2001 | Dimke | |
| 6,410,807 B1 | 6/2002 | Yang et al. | |
| 6,677,468 B1 | 1/2004 | Dimke et al. | |
| 8,318,834 B2 | 11/2012 | Hefner, Jr. et al. | |
| 9,068,039 B2 * | 6/2015 | Hefner, Jr. | ........... C08G 59/022 |
| 2002/0161106 A1 | 10/2002 | Anderson | |
| 2006/0235183 A1 | 10/2006 | Ogura et al. | |
| 2007/0087146 A1 | 4/2007 | Evans et al. | |
| 2007/0117938 A1 | 5/2007 | Martz et al. | |
| 2007/0281179 A1 | 12/2007 | Ambrose et al. | |
| 2011/0039982 A1 | 2/2011 | Hefner, Jr. et al. | |
| 2011/0040046 A1 | 2/2011 | Hefner, Jr. et al. | |
| 2011/0054056 A1 | 3/2011 | Hefner, Jr. et al. | |
| 2013/0144015 A1 * | 6/2013 | Hefner | .......................... 525/524 |
| 2013/0237642 A1 * | 9/2013 | Hefner, Jr. | .................... 523/427 |
| 2013/0302336 A1 * | 11/2013 | Heywood et al. | .......... 424/136.1 |

FOREIGN PATENT DOCUMENTS

| | | |
|---|---|---|
| EP | 0121260 A2 | 10/1984 |
| EP | 0253405 A2 | 1/1988 |
| EP | 0702042 A1 | 3/1996 |
| GB | 1204760 A | 9/1970 |
| JP | 200700915 | 1/2007 |
| WO | 9510556 A1 | 4/1995 |
| WO | 0001779 A1 | 1/2000 |
| WO | 03078512 A1 | 9/2003 |
| WO | 2007078859 A2 | 7/2007 |
| WO | 2008045882 A1 | 4/2008 |
| WO | 2008045884 A1 | 4/2008 |
| WO | 2008045889 A1 | 4/2008 |
| WO | 2008045894 A1 | 4/2008 |
| WO | 2009105938 A1 | 9/2009 |
| WO | 2009142898 A1 | 11/2009 |
| WO | 2009142900 A1 | 11/2009 |
| WO | 2009142901 A1 | 11/2009 |
| WO | 2012044443 A1 | 4/2012 |
| WO | 2012044455 A1 | 4/2012 |
| WO | 2012044458 A1 | 4/2012 |
| WO | 2012050777 A1 | 4/2012 |

OTHER PUBLICATIONS

U.S. Appl. No. 61/388,059, (expired), Oct. 25, 2010.
(Continued)

*Primary Examiner* — Robert Sellers

(57) ABSTRACT

A re-epoxidized polyfunctional epoxy resin composition comprising the reaction product of: (I) an epoxidized polyfunctional epoxy resin oligomeric composition comprising a polyfunctional aliphatic or cycloaliphatic epoxy resin which has been isolated from an epoxy resin product formed as a result of an epoxidation process comprising the reaction of: (i) an aliphatic or cycloaliphatic hydroxyl-containing material; (ii) an epihalohydrin, (iii) a basic-acting substance, in the presence of (iv) a non-Lewis acid catalyst; and (v) optionally, one or more solvents; (II) an epihalohydrin; (III) a basic acting substance; in the presence of (IV) a non-Lewis acid catalyst; and (V) optionally, one or more solvents. A curable epoxy resin composition of the re-epoxidized polyfunctional epoxy resin composition and a thermoset of the curable composition is also disclosed.

2 Claims, 1 Drawing Sheet

(56) References Cited

OTHER PUBLICATIONS

PCT/US2011/050613, International Search Report and Written Opinion, May 1, 2012.
PCT/US2011/050613, International Preliminary Report on Patentability, Jan. 15, 2013.
Dean J. M. et al reported in J. Polym. Sci., Part B: Polym. Phys. 39, 2996, 3010 (2001).
Taira, Kazunari, et al., Journal of the American Chemical Society, Jun. 8, 1984, 7831-7835, V. 106.
White S.R. et al in Nature 409, 794, 797 (2001).
PCT/ US2011/050742, International Preliminary Report on Patentability., Apr. 2, 2013.
PCT/ US2011/050742, International Search Report and Written Opinion of the International Searching Authority., May 16, 2012.
PCT/ US2011/052236 International Preliminary Report on Patentability., Apr. 2, 2013.
PCT/US/2011/052672, International Preliminary Report on Patentability., Apr. 2, 2013.
PCT/US/2011/052672, International Search Report., Dec. 15, 2011.
PCT/US/2011/052672, Written Opinion of the International Searching Authority.
PCT/US2011/049840, International Preliminary Report on Patentability., Apr. 2, 2013.
PCT/US2011/049840, International Search Report., May 11, 2012.
PCT/US2011/049840, Written Opinion of the International Searching Authority., May 11, 2012.
PCT/US2011/050597, International Preliminary Report on Patentability.
PCT/US2011/050597, International Search Report., Jan. 3, 2012.
PCT/US2011/050597, Written Opinion of the International Searching Authority.
PCT/US2011/051291, International Preliminary Report on Patentability., Apr. 2, 2013.
PCT/US2011/051291, International Search Report., Dec. 2, 2011.
PCT/US2011/051291, Written Opinion of the International Searching Authority., Apr. 2, 2013.
PCT/US2011/051482, International Preliminary Report on Patentability, Apr. 2, 2013.
PCT/US2011/051482, International Search Report and Written Opinion of the International Searching Authority., Nov. 24, 2011.
PCT/US2011/052236 International Search Report and Written Opinion of the International Searching Authority, Dec. 6, 2011.

* cited by examiner

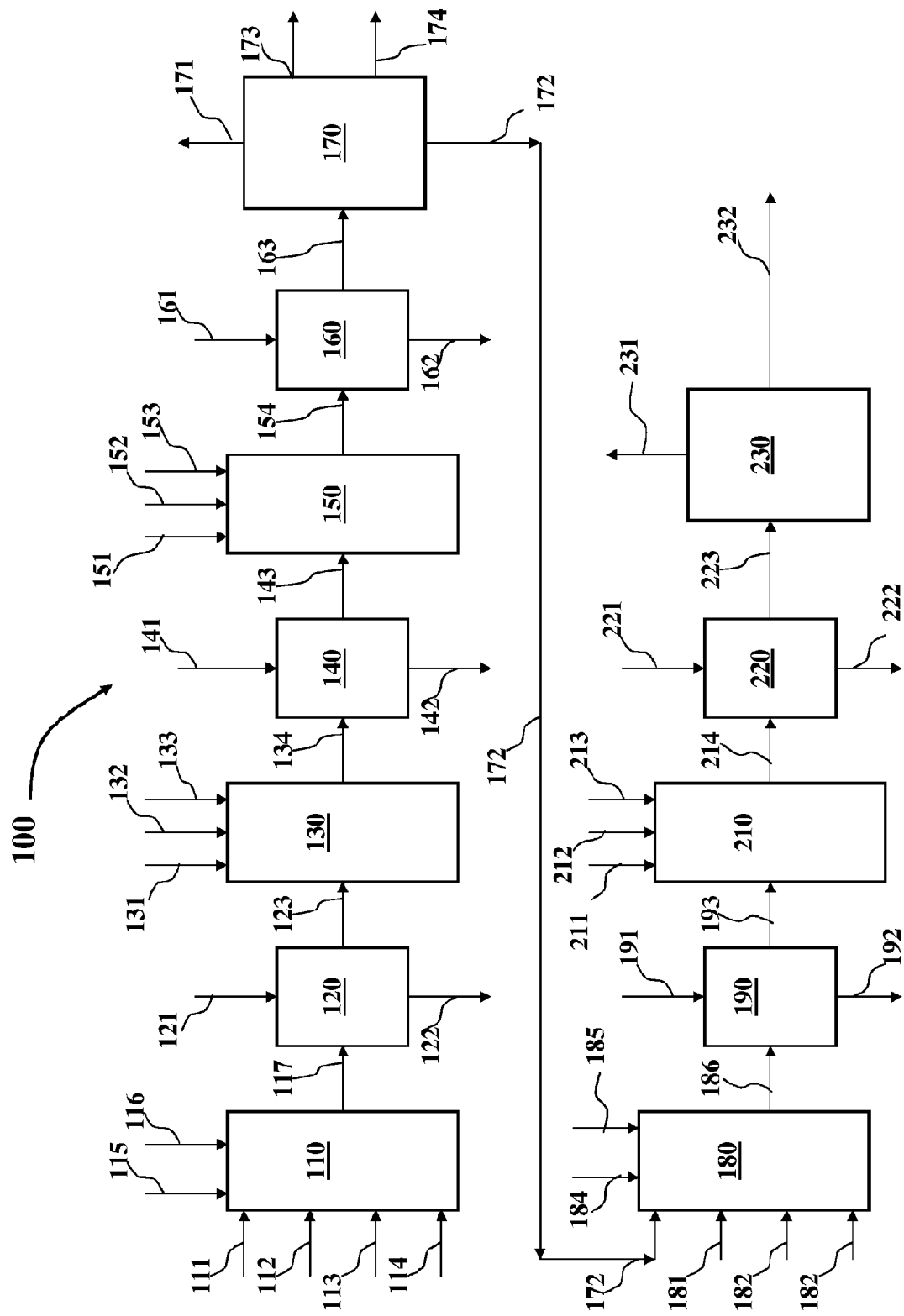

EPOXY RESIN COMPOSITIONS

This application is a non-provisional application claiming priority from the U.S. Provisional Patent Application No. 61/388,064, filed on Sep. 30, 2010, entitled "EPOXY RESIN COMPOSITIONS" the teachings of which are incorporated by reference herein, as if reproduced in full hereinbelow.

BACKGROUND OF THE INVENTION

1. Field of the Invention

The present invention is related an epoxy resin composition prepared by re-epoxidizing a polyfunctional aliphatic and/or cycloaliphatic epoxy resin precursor derived from an oligomer fraction of an epoxy resin of an aliphatic and/or cycloaliphatic hydroxyl-containing material. The present invention is additionally related to thermosettable compositions made from re-epoxidized polyfunctional aliphatic and/or cycloaliphatic epoxy resins and to thermosets made from said thermosettable compositions.

2. Description of Background and Related Art

Epoxidation of aliphatic and cycloaliphatic alcohols is an area of long standing interest, for example as described in EP 0 121 260, incorporated herein by reference. Disclosed in EP 0 121 260 are examples of phase transfer catalyzed epoxidation of aliphatic diols using quaternary ammonium halide catalysts with epichlorohydrin, including cyclohexanedimethanol.

WO 2009/142901, incorporated herein by reference, describes an epoxy resin composition prepared from a mixture of cis-, trans-1,3- and 1,4-cyclohexanedimethanols using several epoxidation processes. WO 2009/142901 also discloses examples of preparing various distilled grades of the monoglycidyl ethers and diglycidyl ethers of cis-, trans-1,3- and 1,4-cyclohexanedimethanols, including a high purity (>99 weight percent [wt %]) diglycidyl ether of cis-, trans-1, 3- and 1,4-cyclohexanedimethanols.

When using the prior art chemistry and processes to manufacture aliphatic and cycloaliphatic epoxy resins via epoxidation of aliphatic and cycloaliphatic hydroxyl-containing materials using an epihalohydrin, it is difficult, if not impossible, to drive to full conversion; and the processes produce significant quantities of oligomeric co-products (as much as 25 wt %-40 wt % of the epoxy resin composition). The components of the epoxy resin may include for example unconverted aliphatic and cycloaliphatic hydroxyl containing material reactant, monoglycidyl ether, diglycidyl ether, oligomeric co-products, and the like. While various methods, such as, for example, distillation, are operable for removing the undesirable oligomeric co-products from the desired high purity diglycidyl ether of cis-, trans-1,3- and 1,4-cyclohexanedimethanols, no satisfactory solution exists for handling the resulting separated and isolated oligomeric co-products. The solution to date has been to use the as produced mixture of the aliphatic and cycloaliphatic epoxy resins and the oligomeric co-products together as a reactive diluent for other epoxy resins where the oligomeric co-products are simply carried into the total diluent and epoxy resin composition. Problems with this approach include preparing an epoxy resin composition having a higher than desirable viscosity induced by the presence of the oligomeric co-products; and having a reduced reactivity with curing agents.

In view of the problems with the prior art processes, it would be highly desirable to be able to fractionate an aliphatic or cycloaliphatic epoxy resin into monoglycidyl ether, diglycidyl ether, and the like, such that any residual oligomeric co-products fraction can be advantageously utilized in subsequent processes to provide novel thermosettable compositions and thermosets based on the residual oligomeric co-products fraction. Such a process and thermosettable compositions and thermosets therefrom are described in co-pending U.S. Patent Application Ser. No. 61/388,059, entitled "THERMOSETTABLE COMPOSITIONS AND THERMOSETS THEREFROM," filed of even date herewith by Robert Hefner, Jr., incorporated herein by reference.

While the thermosettable compositions and thermosets based on the residual oligomeric co-products fraction provide numerous benefits, there is significant room for improvement of the properties provided by said compositions. Thus, it would be highly desirable to be able to fractionate an aliphatic or cycloaliphatic epoxy resin into monoglycidyl ether, diglycidyl ether, and the like, while simultaneously providing novel epoxy resins, thermosettable compositions and thermosets thereof with improved properties based on the re-epoxidation of the residual oligomeric fraction.

SUMMARY OF THE INVENTION

A "residual oligomeric product" herein means an oligomeric fraction which is co-produced during an epoxidation process for producing an aliphatic or cycloaliphatic epoxy resin product; wherein the co-produced oligomeric fraction and the aliphatic or cycloaliphatic epoxy resin product resultant mixture after the epoxidation process is subjected to a subsequent separation process such that the co-produced oligomeric fraction is separated and isolated from the aliphatic or cycloaliphatic epoxy resin product. The separation process can be carried out by a known means such as for example a distillation unit operation. Once the co-produced oligomeric fraction is separated from the aliphatic or cycloaliphatic epoxy resin product, for example by distillation, the resulting separated/isolated oligomeric fraction product, typically the residual bottoms material of a distillation process, comprises the residual oligomeric product useful in the present invention.

Accordingly, one embodiment of the present invention is directed to an epoxy resin composition including the reaction product of (I) a residual oligomeric product, wherein the residual oligomeric product comprises a polyfunctional aliphatic or cycloaliphatic epoxy (PACE) resin, (II) an epihalohydrin, and (III) a basic-acting substance, in the presence of (IV) a non-Lewis acid catalyst, and (V) optionally, one or more solvents.

In another embodiment of the present invention, the above epoxy resin composition is prepared by the process of epoxidizing further (i.e., "re-epoxidizing") a PACE resin to produce the novel compositions of the present invention. The re-epoxidation process of the present invention converts hydroxyl groups present in the PACE resin to glycidyl ether groups providing increased thermosettable functionality.

Another embodiment of the present invention is directed to a thermosettable (curable) epoxy resin composition comprising (a) the re-epoxidized epoxy resin composition described above, (b) an epoxy resin curing agent and/or a catalyst, and (c) optionally, an epoxy resin compound other than the epoxy resin composition (a).

Another aspect of the present invention is directed to a process of partially thermosetting (B-staging) or completely thermosetting the above thermosettable epoxy resin compositions.

A further aspect of the present invention is directed to a process of preparing the above thermosettable epoxy resin.

Still another embodiment of the present invention is directed to a thermoset article prepared by curing the above thermosettable epoxy resin composition.

Upon curing (thermosetting) the epoxy resin composition, a higher crosslink density of the cured thermoset matrix can result. The higher crosslink density can favorably improve the resulting cured product properties such as its glass transition temperature, resistance to moisture, resistance to solvents, toughness, and the like. The conversion of hydroxyl groups to glycidyl ether groups is especially desirable to increase resistance to moisture in the cured epoxy resin and increase glass transition temperature as well as reduce viscosity of the liquid epoxy resin. Additionally, the process of the present invention serves to decrease the amount of undesirable hydrolyzable chloride, if present, via dehydrochlorination of any chlorohydrin groups in the resultant oligomer fraction.

BRIEF DESCRIPTION OF THE DRAWINGS

For the purpose of illustrating the present invention, the drawings show several embodiments of the present invention. However, it should be understood that the present invention is not limited to the precise arrangements and instrumentalities shown in the drawings.

FIG. 1 is a schematic flow diagram showing a process of the present invention in the production of a re-epoxidized epoxy resin product.

DETAILED DESCRIPTION OF THE INVENTION

U.S. Pat. No. 9,068,039 discloses a curable polyfunctional aliphatic/cycloaliphatic epoxy resin composition, thermosets thereof, and applications therefor such as weatherable coatings. Also, as disclosed in the above patent application, because epoxy resins of aliphatic or cycloaliphatic diols comprise as much as 25 percent (%)-40% oligomer fraction, in order for any project requiring purified diglycidyl ether to be commercially successful, value must be recovered from this oligomer fraction.

In the present invention, the oligomeric components isolated from a PACE resin are epoxidized further (re-epoxidized) to produce the novel compositions of the present invention. This re-epoxidation process converts hydroxyl groups present in the PACE resin to glycidyl ether groups providing increased thermosettable functionality. Upon curing (thermosetting) this can result in higher crosslink density of the cured thermoset matrix. This can favorably increase glass transition temperature, increase resistance to moisture and solvents, increase toughness, and the like. The conversion of hydroxyl groups to glycidyl ether groups is especially desirable to increase resistance to moisture in the cured epoxy resin, as well as reduce viscosity of the liquid epoxy resin. Additionally, the re-epoxidation process serves to decrease the amount of undesirable hydrolyzable chloride, if present, via dehydrochlorination of any chlorohydrin groups in the PACE resin.

The re-epoxidation process of the present invention is expected to be broadly applicable to upgrade the residual oligomeric product comprising a polyfunctional aliphatic or cycloaliphatic epoxy resin which may be isolated from the numerous commercially available aliphatic and cycloaliphatic epoxy resins. Of particular interest are the aliphatic and cycloaliphatic epoxy resins produced via non-Lewis acid catalyzed epoxidation of an aliphatic and/or cycloaliphatic hydroxyl-containing compound or material with an epihalohydrin because of the significant amount of unreacted hydroxyl groups which can be present in the residual oligomeric product fraction isolated from said epoxy resin concomitant with the minor amount of bound chloromethyl groups present.

The process of the present invention would allow for separation of the very low viscosity diglycidyl ether useful for advancement reactions if sufficiently pure as well as a low viscosity reactive diluent for epoxy resins. The remaining oligomer fraction is recovered and re-epoxidized as per the disclosure of the present invention.

One objective of the present invention is to provide a process including re-epoxidizing an oligomeric epoxy resin fraction remaining after a distillation unit operation is carried out to substantially recover a high purity diglycidyl ether product.

Another objective of the present invention is to use the resultant re-epoxidized epoxy resin composition produced from the re-epoxidation process above, to produce thermosettable compositions and thermosets from said thermosettable compositions. This will provide products for further use in various applications such as maintenance coatings.

As noted above, the present invention is directed to a novel epoxy resin composition which is a polyfunctional aliphatic and/or cycloaliphatic epoxy resin composition prepared by re-epoxidizing oligomeric products present in an oligomer fraction separated and isolated from an epoxy resin formed by the epoxidation of an aliphatic or cycloaliphatic hydroxyl containing material.

One broad embodiment of the present invention comprises a re-epoxidized epoxy resin composition; wherein the re-epoxidized epoxy resin composition comprises the reaction product of epoxidizing (re-epoxidizing) a PACE resin which has been separated and isolated from an aliphatic or cycloaliphatic epoxy resin. For example, one embodiment of the present invention comprises a re-epoxidized epoxy resin composition including the reaction product of (I) a PACE resin, (II) an epihalohydrin, and (III) a basic-acting substance, in the presence of (IV) a non-Lewis acid catalyst, and (V) optionally, one or more solvents.

As an illustration of a more specific embodiment of the present invention, the epoxy resin of an aliphatic or cycloaliphatic diol, such as, for example, a cis-, trans-1,3- and 1,4-cyclohexanedimethanol (e.g. a commercial cyclohexanedimethanol sold under the trademark of UNOXOL™ Diol by The Dow Chemical Company) from a non-Lewis acid catalyzed epoxidation process, typically consists of a minor amount of unreacted aliphatic or cycloaliphatic diol, monoglycidyl ether, diglycidyl ether, and oligomeric products. Distillation methods are typically employed to remove the unreacted aliphatic or cycloaliphatic diol, monoglycidyl ether, and any other lower boiling materials. [UNOXOL™ cyclic dialcohol is a registered trademark of Union Carbide Corporation.]

The diglycidyl ether is then removed as a product with high enough purity, typically 98% or greater, for use in advancement chemistry. After the diglycidyl ether is substantially removed, the polyfunctional oligomeric product remaining in the distillation pot is recovered. Thus, this specific embodiment of the present invention is based on the production of a high purity (≥98%) cycloaliphatic diglycidyl ether, specifically, the diglycidyl ether of UNOXOL™ Diol. For the aforementioned advancement reaction, the oligomeric products must be removed or else their polyfunctionality induces gelation before advancement can be completed.

While U.S. Pat. No. 9,068,039 provides novel compositions of the PACE resin with curing agents, thermosets thereof, and applications for the resultant thermosets, the present invention provides novel polyfunctional oligomeric epoxy resins which are obtained via re-epoxidation. The present invention additionally provides enhanced performance from said re-epoxidized PACE resins. In one broad embodiment, the present invention may be applied to any epoxy resin of an aliphatic or cycloaliphatic hydroxyl-containing material or compound. The process of the present invention can benefit and be applied widely to existing numerous commercial processes that produce aliphatic and cycloaliphatic epoxy resins.

Component (I) is a residual oligomeric product; wherein the residual oligomeric product comprises a PACE resin. For example the PACE resin can be a co-product (or a secondary product) resulting from a first epoxidation reaction carried out to produce a primary epoxy resin product. The PACE resin co-product is separated from and isolated from the primary epoxy resin product formed as a result of the epoxidation process. The epoxidation process which produces the primary epoxy resin product and the PACE resin co-product comprises a reaction employing the following components: (A) an aliphatic or cycloaliphatic hydroxyl-containing material, (B) an epihalohydrin, (C) a basic-acting substance, (D) a non-Lewis acid catalyst, and (E) optionally, one or more solvents The oligomeric product or PACE resin in general is an epoxy resin precursor as one reactant for the re-epoxidation process of the present invention. The PACE resin is obtained via isolation from an aliphatic or cycloaliphatic epoxy resin formed by the epoxidation of (i) an aliphatic or cycloaliphatic hydroxyl containing material using (ii) an epihalohydrin, (iii) a basic-acting substance, (iv) a non-Lewis acid catalyst, and (v) optionally one or more solvents.

The term "aliphatic or cycloaliphatic polyfunctional epoxy resin", also referred to herein interchangeably as "oligomeric product or co-product" or simply "oligomer", as used herein means the product isolated from an epoxy resin formed by the epoxidation of (i) an aliphatic or cycloaliphatic hydroxyl containing material using (ii) an epihalohydrin, (iii) a basic-acting substance, (iv) a non-Lewis acid catalyst, and (v) optionally one or more solvents. Said isolated product comprises the product remaining after removal of all (1) "light" components, such as, for example, solvents used in the epoxidation reaction, if any, unreacted epihalohydrin, and co-products such as di(epoxypropyl)ether; (2) unreacted aliphatic or cycloaliphatic hydroxyl containing material, if any; removal of (3) partially epoxidized aliphatic or cycloaliphatic hydroxyl containing material, such as, for example, monoglycidyl ether; and substantial removal of (4) fully epoxidized aliphatic or cycloaliphatic hydroxyl containing material, such as, for example, diglycidyl ether, such that the PACE resin product remaining contains no more than 20 wt % of said fully epoxidized aliphatic or cycloaliphatic hydroxyl containing material.

Some representative specific classes of aliphatic or cycloaliphatic hydroxyl-containing reactants, component (A) or (i), which may be employed in the epoxidation to produce the PACE resin precursor to the re-epoxidation product of the present invention include for example the following:

The aliphatic or cycloaliphatic hydroxyl-containing reactant useful in the present invention may include for example cyclohexanedialkanols and cyclohexenedialkanols having the following chemical structures:

(a) Cyclohexanedialkanols and Cyclohexenedialkanols

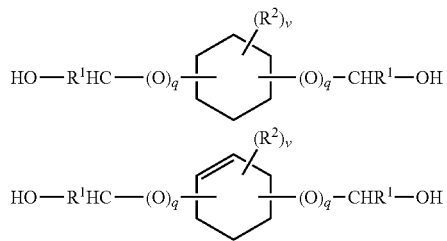

where each $R^1$ is independently —H or a $C_1$ to $C_6$ alkylene radical (saturated divalent aliphatic hydrocarbon radical), each $R^2$ is independently a $C_1$ to $C_{12}$ alkyl or alkoxy radical, a cycloalkyl or cycloalkoxy radical, or an aromatic ring or inertly substituted aromatic ring; each q independently has a value of 0 or 1; and v has a value of 0 to 2.

Representative examples of the cyclohexanedialkanols and cyclohexenedialkanols include UNOXOL™ Diol (cis-, trans-1,3- and 1,4-cyclohexanedimethanol), cis-, trans-1,2-cyclohexanedimethanol; cis-, trans-1,3-cyclohexanedimethanol; cis-, trans-1,4-cyclohexanedimethanol; a methyl substituted cyclohexanedimethanol, such as, for example, a 4-methyl-1,2-cyclohexanedimethanol or 4-methyl-1,1-cyclohexanedimethanol; 1,1-cyclohexanedimethanol; a cyclohexenedimethanol such as, for example, 3-cyclohexene-1,1-dimethanol; 3-cyclohexene-1,1-dimethanol, 6-methyl-; 4,6-dimethyl-3-cyclohexene-1,1-dimethanol; cyclohex-2-ene-1,1-dimethanol; 1,1-cyclohexanediethanol; 1,4-bis(2-hydroxyethoxy)cyclohexane; 1,4-cyclohexanediethanol; mixtures thereof and the like. Included within this class of epoxy resins are the cyclohexanedioxyalkanols and cyclohexenedioxyalkanols, where at least one q has a value of 1. Specific examples include 1,4-bis(2-hydroxyethyloxy)cyclohexane- and 1,4-bis(2-hydroxyethyloxy)cyclohex-2-ene. All possible geometric isomers are intended by the formulas and in the aforementioned list, even if the isomers are not explicitly shown or given.

A representative synthesis of 1,1-cyclohexanedimethanol is given by Manea, et al, Paint and Coatings Industry, Aug. 1, 2006, incorporated herein by reference in its entirety. A representative synthesis of 3-cyclohexene-1,1-dimethanol is described in U.S. Pat. No. 6,410,807, incorporated herein by reference.

UNOXOL™ Diol (cis-, trans-1,3- and 1,4-cyclohexanedimethanol) is a preferred cyclohexanedialkanol. As used herein, the term "cis-, trans-1,3- and -1,4-cyclohexanedimethylether moiety" means a structure or a blend of chemical structures comprising four geometric isomers, a cis-1,3-cyclohexanedimethylether, a trans-1,3-cyclohexanedimethylether structure, a cis-1,4-cyclohexanedimethylether, and a trans-1,4-cyclohexanedimethylether, within an epoxy resin. The four geometric isomers are shown in the following structures:

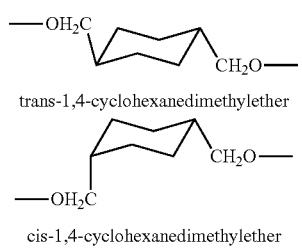

trans-1,4-cyclohexanedimethylether cis-1,4-cyclohexanedimethylether

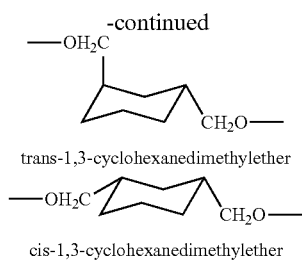

trans-1,3-cyclohexanedimethylether cis-1,3-cyclohexanedimethylether

A detailed description of the epoxy resins comprising the cis-, trans-1,3- and 1,4-cyclohexanedimethylether moiety and the processes for preparing the same is provided in the aforementioned WO2009/142901. Phase transfer catalyzed epoxidation of aliphatic diols using quaternary ammonium halide catalysts with epichlorohydrin to produce aliphatic epoxy resins with properties that are superior to the corresponding aliphatic epoxy resins produced via Lewis acid catalyzed coupling with epichlorohydrin is described in aforementioned EP Patent No. 0 121 260. Included are epoxy resins prepared from cyclohexanedimethanol and dicyclopentadienedimethanol (isomers unspecified).

The aliphatic or cycloaliphatic hydroxyl-containing reactant useful in the present invention may include for example one or more cyclohexanolmonoalkanols and cyclohexenolmonoalkanols having the following chemical structures:

(b) Cyclohexanolmonoalkanols and Cyclohexenolmonoalkanols

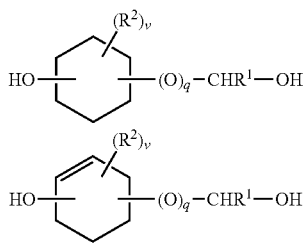

where each $R^1$, $R^2$, q and v are as hereinbefore defined.

Representative examples of the cyclohexanolmonoalkanols and cyclohexenolmonoalkanols which are aliphatic/cycloaliphatic hybrid diol structures containing one cyclohexanol or cyclohexenol moiety and one monoalkanol moiety, such as, for example, a monomethanol moiety, include, for example, 1-(hydroxymethyl)-cyclohexanol, 1-(hydroxymethyl)cyclohex-3-enol, 3-hydroxymethylcyclohexanol, 4-hydroxymethylcyclohexanol, rac-1-isopropyl-4-methyl-2-cyclohexene-1alpha,2alpha-diol; 5beta-isopropyl-2-methyl-3-cyclohexene-1alpha,2alpha-diol; 2-hydroxymethyl-1,3,3-trimethyl-cyclohexanol; cyclohexanol, 1-(2-hydroxyethoxy); mixtures thereof and the like. All possible geometric isomers are intended by the formulas and in the aforementioned list, even if the isomers are not explicitly shown or given.

Another example of such compounds is trans-2-(hydroxymethyl)cyclohexanol prepared by Prins reaction on cyclohexane by Kazunari Taira et al, Journal of the American Chemical Society, 106, 7831-7835 (1984), incorporated herein by reference. A second example is 1-phenyl-cis-2-hydroxymethyl-r-1-cyclohexanol disclosed in U.S. Pat. No. 4,125,558, incorporated herein by reference. A third example is trans-4-(hydroxymethyl)cyclohexanol reported by Tamao et al., Organic Syntheses, Collective Volume 8, p. 315, Annual Volume 69, p. 96, incorporated herein by reference.

The aliphatic or cycloaliphatic hydroxyl-containing reactant useful in the present invention may include for example one or more decahydronaphthalenedialkanols, octahydronaphthalenedialkanols and 1,2,3,4-tetrahydronaphthalenedialkanols having the following chemical structures:

(c) Decahydronaphthalenedialkanols, Octahydronaphthalenedialkanols and 1,2,3,4-Tetrahydronaphthalenedialkanols

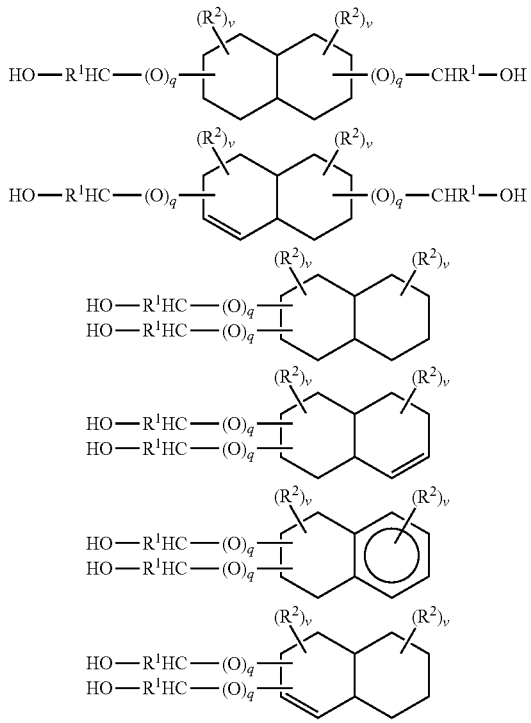

where each $R^1$, $R^2$, q and v are as hereinbefore defined.

Representative examples of the decahydronaphthalenedialkanols, octahydronaphthalenedialkanols and 1,2,3,4-tetrahydronaphthalenedialkanols containing one decahydronaphthalenedialkanol, octahydronaphthalenedialkanol or 1,2,3,4-tetrahydronaphthalenedialkanol moiety, include 1,2-decahydronaphthalenedimethanol; 1,3-decahydronaphthalenedimethanol; 1,4-decahydronaphthalenedimethanol; 1,5-decahydronaphthalenedimethanol; 1,6-decahydronaphthalenedimethanol; 2,7-decahydronaphthalenedimethanol; 1,2,3,4-tetrahydronaphthalenedimethanol (tetralin dimethanol); 1,2-octahydronaphthalenedimethanol; 2,7-octahydronaphthalenedimethanol; 4-methyl-1,2-decahydronaphthalenedimethanol; 4,5-dimethyl-2,7-decahydronaphthalenedimethanol; 1,2-decahydronaphthalenediethanol; 2,7-decahydronaphthalenediethanol; mixtures thereof and the like. All possible geometric isomers are intended by the formulas and in the aforementioned list, even if the isomers are not explicitly shown or given.

While not shown by the structures given above, it is intended that the hybrid diol structures also be included where one monoalkanol moiety is attached to a cycloaliphatic ring and one hydroxyl moiety is directly attached to a cycloaliphatic ring. One example of said hybrid structures would be 1-hydroxy-2-hydroxymethyldecahydronaphthalene.

The aliphatic or cycloaliphatic hydroxyl-containing reactant useful in the present invention may include for example one or more bicyclohexanedialkanols or bicyclohexanolmonoalkanols having the following chemical structures:

(d) Bicyclohexanedialkanols or Bicyclohexanolmonoalkanols

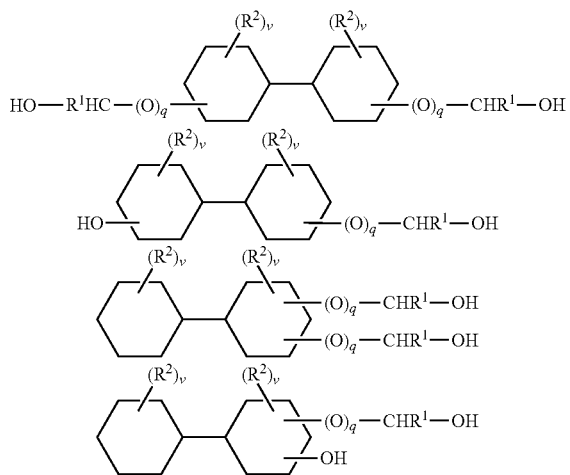

where each $R^1$, $R^2$, q and v are as hereinbefore defined.

Representative examples of the bicyclohexanedialkanols or bicyclohexanolmonoalkanols include bicyclohexane-4,4'-dimethanol; bicyclohexane-1,1'-dimethanol; bicyclohexane-1,2-dimethanol, bicyclohexane-4,4'-diethanol; bicyclohexane-1-hydroxy-1'-hydroxymethyl; bicyclohexane-4-hydroxy-4'-hydroxymethyl; mixtures thereof and the like. All possible geometric isomers are intended by the formulas and in the aforementioned list, even if the isomers are not explicitly shown or given.

While not shown by the structures given above, it is intended that epoxy resins of bicyclohexenedialkanols or bicyclohexenolmonoalkanols be included where either one or both rings may contain a single unsaturation. One example of said bicyclohexene structures would be the epoxy resin of bicyclohexene-1,1'-dimethanol.

The aliphatic or cycloaliphatic hydroxyl-containing reactant useful in the present invention may include for example one or more bridged cyclohexanols having the following chemical structures:

(e) Bridged Cyclohexanols

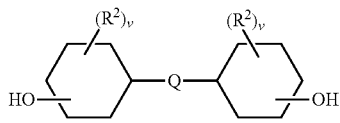

where each Q is a $C_1$ to $C_{12}$ alkylene radical (saturated divalent aliphatic hydrocarbon radical), O, S, O=S=O, S=O, C=O, $R^3NC$=O; $R^3$ is —H or a $C_1$ to $C_6$ alkyl radical (saturated monovalent aliphatic hydrocarbon radical); $R^2$ and v are as hereinbefore defined.

Representative examples of the bridged cyclohexanols include the following compounds where the aromatic rings have been hydrogenated to cyclohexane rings: bisphenol A (4,4'-isopropylidenediphenol), bisphenol F (4,4'-dihydroxydiphenylmethane), 4,4'-dihydroxydiphenylsulfone; 4,4'-dihydroxybenzanilide; 1,1'-bis(4-hydroxyphenyl)cyclohexane; 4,4'-dihydroxydiphenyl oxide; 4,4'-dihydroxybenzophenone; 1,1-bis(4-hydroxyphenyl)-1-phenylethane; 4,4'-bis(4(4-hydroxyphenoxy)-phenylsulfone)diphenyl ether; 2,2'-sulfonyldiphenol; 4,4'-thiodiphenol; dicyclopentadiene diphenol.

(f) Other Cycloaliphatic and Polycycloaliphatic Diols, Monol Monoalkanols, or Dialkanols Most any cycloaliphatic or polycycloaliphatic diol, monol monoalkanol or dialkanol may be employed in the epoxidation process. Representative examples include the dicyclopentadienedimethanols, the norbornenedimethanols, the norbornanedimethanols, the cyclooctanedimethanols, the cyclooctenedimethanols, the cyclooctadienedimethanols, the pentacyclodecanedimethanols, the bicyclooctanedimethanols, the tricycledecanedimethanols, the bicycloheptenedimethanols, the dicyclopentadienediols, the norbornenediols, the norbornanediols, the cyclooctanediols, the cyclooctenediols, the cyclooctadienediols, the cyclohexanediols, the cyclohexenediols, cyclopentane-1,3-diol; bicyclopentane-1,1'-diol; decahydronaphthalene-1,5-diol; trans, trans-2,6-dimethyl-2,6-octadiene-1,8-diol; 5-methylol-5-ethyl-2-(1,1-dimethyl-2-hydroxyethyl)-1,3-dioxane; 3,9-bis (1,1-dimethyl-2-hydroxyethyl)-2,4,8,10-tetraoxaspiro[5.5] undecane; 3-methyl-2,2-norbornanedimethanol; 5-norbornene-2,3-dimethanol; norbornane-2,3-trans-dimethanol; perhydro-1,4:5,8-dimethano naphthalene-2,3-trans-dimethanol; perhydro-1,4:5,8:9,10-trimethano anthracene-2,3-trans-dimethanol; and 5-norbornene-2,3-dimethanol; norbornanolmonomethanols; and norbornenediols.

Preparation of norbornane-2,3-trans-dimethanol; perhydro-1,4:5,8-dimethanonaphthalene-2,3-trans-dimethanol; and perhydro-1,4:5,8:9,10-trimethanoanthracene-2,3-trans-dimethanol are reported by Wilson et al., Journal of Polymer Science Polymer Chemistry Edition, volume 10, 3191-3204 (1972), incorporated herein by reference. Preparation of 5-norbornene-2,3-dimethanol is reported by Hitoshi Nakamura et al, Macromolecules, 23, 3032-3035 (1990), incorporated herein by reference.

(g) Aliphatic Hydroxyl-Containing Materials

Most any aliphatic hydroxyl containing reactant may be employed in the epoxidation process. Representative of the aliphatic hydroxyl containing reactants include alkoxylated phenolic reactants, such as, for example, ethoxylated catechol, ethoxylated resorcinol, ethoxylated hydroquinone, and ethoxylated bisphenol A. Alkoxylation products of the hydrogenated aromatic phenolic reactants include ethoxylated hydrogenated bisphenol A. Other aliphatic hydroxyl containing reactants include neopentyl glycol, trimethylol propane, ethylene glycol, propylene glycol, triethylene glycol, higher alkoxylated ethylene glycols, pentaerythritol, 1,4-butanediol; 1,6-hexanediol; and 1,12-dodecandiol.

Epihalohydrins which may be employed in the epoxidation to produce the PACE resin precursor to the re-epoxidation product of the present invention and also in the re-epoxidation process, include, for example, epichlorohydrin, epibromohydrin, epiiodohydrin, methylepichlorohydrin, methylepibromohydrin, methylepiiodohydrin, and any combination thereof. Epichlorohydrin is the preferred epihalohydrin.

The ratio of the epihalohydrin to the aliphatic or cycloaliphatic hydroxyl containing material for the epoxidation process to produce the PACE resin precursor is generally from about 1:1 to about 25:1, preferably from about 1.8:1 to about 10:1, and more preferably from about 2:1 to about 5:1 equivalents of epihalohydrin per hydroxyl group in the aliphatic or cycloaliphatic hydroxyl containing material. The term "hydroxyl group" used herein refers to the hydroxyl groups derived from the aliphatic or cycloaliphatic hydroxyl containing material. Thus the hydroxyl group differs from a secondary hydroxyl group formed during the process of the forming the halohydrin intermediate to the aliphatic or cycloaliphatic hydroxyl containing material.

For the re-epoxidation of the PACE resin precursor, the ratio of the epihalohydrin per hydroxyl group is generally from about 1:1 to about 100:1, preferably from about 1.8:1 to about 20:1, and more preferably from about 2:1 to about 10:1 equivalents of epihalohydrin per hydroxyl group be employed, where the term "hydroxyl group" includes any hydroxyl groups derived from the aliphatic or cycloaliphatic hydroxyl containing material which have not been epoxidized, as well as the secondary hydroxyl groups formed during the process of the forming the halohydrin intermediate to the aliphatic or cycloaliphatic hydroxyl containing material which have not been epoxidized.

Basic acting substances which may be employed in the epoxidation to produce the PACE resin precursor to the re-epoxidation product of the present invention and also in the re-epoxidation process include alkali metal hydroxides, alkaline earth metal hydroxides, carbonates, bicarbonates, and any mixture thereof, and the like. More specific examples of the basic acting substance include sodium hydroxide, potassium hydroxide, lithium hydroxide, calcium hydroxide, barium hydroxide, magnesium hydroxide, manganese hydroxide, sodium carbonate, potassium carbonate, lithium carbonate, calcium carbonate, barium carbonate, magnesium carbonate, manganese carbonate, sodium bicarbonate, potassium bicarbonate, magnesium bicarbonate, lithium bicarbonate, calcium bicarbonate, barium bicarbonate, manganese bicarbonate, and any combination thereof. Sodium hydroxide and/or potassium hydroxide are the preferred basic acting substance.

Non-Lewis acid catalysts which may be employed in the epoxidation to produce the PACE resin precursor to the re-epoxidation product of the present invention and also in the re-epoxidation process include, for example, ammonium, phosphonium, or sulfonium salts. More specific examples of the catalyst include salts of the following ammonium, phosphonium and sulfonium cations: benzyltributylammonium, benzyltriethylammonium, benzyltrimethylammonium, tetrabutylammonium, tetraoctylammonium, tetramethylammonium, tetrabutylphosphonium, ethyltriphenylphosphonium, triphenylsulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, 4-tert-butoxycarbonylmethyloxy-phenyldiphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-n-hexyloxy-3,5-dimethylphenyl)diphenylsulfonium, dimethyl(2-naphthyl)sulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium. Preferred cations are triphenylsulfonium, 4-tert-butylphenyldiphenylsulfonium, 4-tert-butoxyphenyldiphenylsulfonium, tris(4-tert-butylphenyl)sulfonium, tris(4-tert-butoxyphenyl)sulfonium, dimethylphenylsulfonium, and any combination thereof. Suitable quaternary phosphonium catalysts also include, for example, the quaternary phosphonium compounds disclosed in U.S. Pat. Nos. 3,948,855; 3,477,990 and 3,341,580; and Canadian Patent No. 858,648, all of which are incorporated herein by reference. Benzyltriethylammonium halides are the preferred catalyst, with benzyltriethylammonium chloride being most preferred.

While the amount of catalyst may vary due to factors such as reaction time and reaction temperature, the lowest amount of catalyst required to produce the desired effect is preferred. In general, the catalyst may be used in an amount of from about 0.5 wt % to about 25 wt %, preferably, from about 1 wt % to about 18 wt %, and more preferably, from about 2 wt % to about 12 wt %, based on the total weight of the aliphatic or cycloaliphatic hydroxyl containing material epoxidized to produce the PACE resin precursor to the re-epoxidation product of the present invention and also in the re-epoxidation process.

The epihalohydrin may function as both a solvent and a reactant in the epoxidation. Alternatively, a solvent other than the epihalohydrin may also be used in the process for preparing the PACE resin (A). The solvent other than the epihalohydrin should be inert to any materials used in the process of preparing the PACE resin (A), including for example, reactants, catalysts, intermediate products formed during the process, and final products. Solvents which may optionally be employed in the epoxidation process include, for example, aliphatic and aromatic hydrocarbons, halogenated aliphatic hydrocarbons, aliphatic ethers, aliphatic nitriles, cyclic ethers, ketones, amides, sulfoxides, tertiary aliphatic alcohols, and any combination thereof.

Particularly preferred solvents include pentane, hexane, octane, toluene, xylene, methylethylketone, methylisobutylketone, dimethylsulfoxide, diethyl ether, tetrahydrofuran, 1,4-dioxane, dichloromethane, chloroform, ethylene dichloride, methyl chloroform, ethylene glycol dimethyl ether, acetonitrile, tertiary-butanol, N,N-dimethylformamide; N,N-dimethylacetamide; and any combination thereof.

If the solvent other than the epihalohydrin is employed in the epoxidation process, the minimum amount of solvent needed to achieve the desired result is preferred. In general, the solvent may be present in the process from about 5 wt % to about 250 wt %, preferably, about 20 wt % to about 180 wt %, and more preferably, about 40 wt % to about 120 wt %, based on the total weight of the aliphatic or cycloaliphatic hydroxyl containing material. The solvent may be removed from the final product at the completion of the reaction of forming the epoxy resin using conventional methods, such as vacuum distillation.

A specific example of the PACE resin is the aliphatic/cycloaliphatic polyfunctional epoxy resin isolated from the epoxy resin of cis-, trans-1,3- and 1,4-cyclohexanedimethanol. It is to be understood that the PACE resin comprises multiple components. For the PACE resin isolated from the epoxy resin of cis-, trans-1,3- and 1,4-cyclohexanedimethanol, the following components have been identified and may or may not be present in the individual products depending on the chemistry and processing employed to produce said epoxy resin (geometrical isomers and substitution are not shown in the chemical structures, the multiple geometrical isomers that are present are not given by the chemical names, other unidentified components may be present):

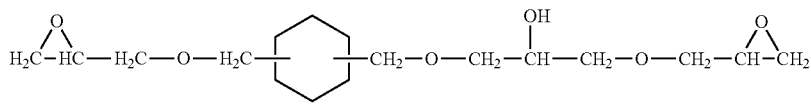

2-propanol, 1-(oxiranylmethoxy)-3-[[3(or 4)-
[(oxiranylmethoxy)methyl]cyclohexyl]methoxy]-

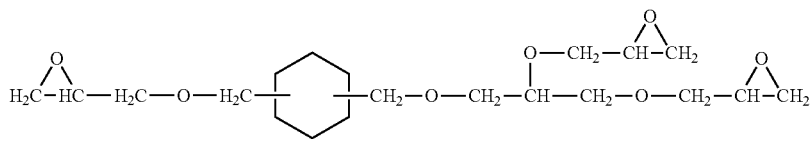

oxirane, 2-[[[3(or 4)-[[2,3-
bis(oxiranylmethoxy)propoxy]methyl]cyclohexyl]methoxy]methyl]-

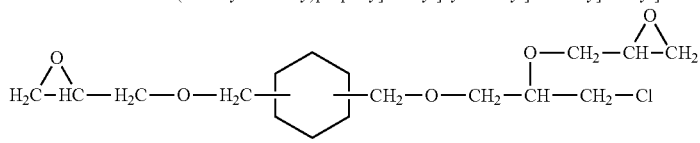

oxirane, 2-[[2-chloro-1-[[[3(or 4)-
[(oxiranylmethoxy)methyl]cyclohexyl]methoxy]methyl]ethoxy]methyl]-

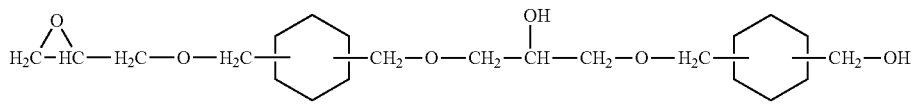

cyclohexanemethanol, 3(or 4)-[[2-hydroxy-3-[[3(or 4)-
[(oxiranylmethoxy)methyl]cyclohexyl]methoxy]propoxy]methyl]-

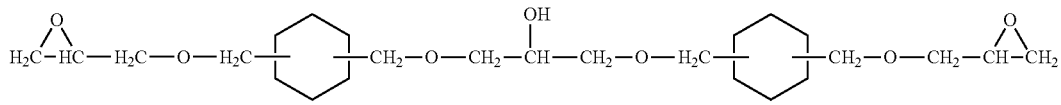

2-propanol, 1,3-bis[[3(or 4)-[(oxiranylmethoxy)methyl]cyclohexyl]methoxy]-

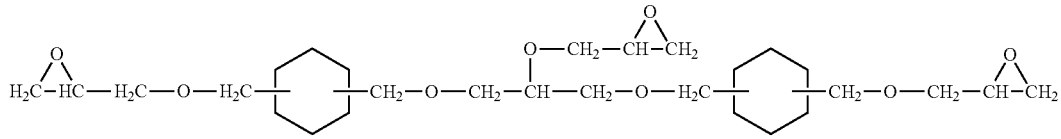

oxirane, 2-[[2-[[3(or 4)-[(oxiranylmethoxy)methyl]cyclohexyl]methoxy]-1-[[[3(or 4)-
[(oxiranylmethoxy)methyl]cyclohexyl]methoxy]methyl]ethoxy]methyl]-

A minor amount of 3 isomeric monochloro compounds co-elute with this latter triglycidyl ether.

Re-epoxidation of the PACE resin is used to beneficially modify the distribution of the components comprising said epoxy resin. Thus in the present specific example of the new compositions from the re-epoxidation of the PACE resin, the re-epoxidation process converts the diglycidyl ethers with a secondary hydroxyl group in their backbone to the corresponding triglycidyl ethers:

While the goal of the re-epoxidation process for most intended applications would be to fully convert the monohydroxy functional diglycidyl ethers to the corresponding triglycidyl ethers, respectively, via selective epoxidation of the secondary hydroxyl groups in the respective backbones, it is also operable to only partially convert these monohydroxy functional diglycidyl ethers to the corresponding triglycidyl ethers.

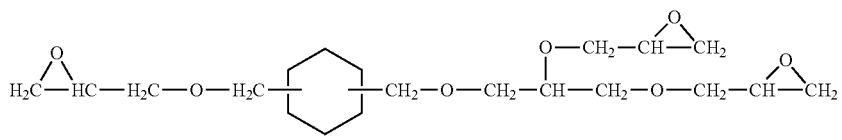

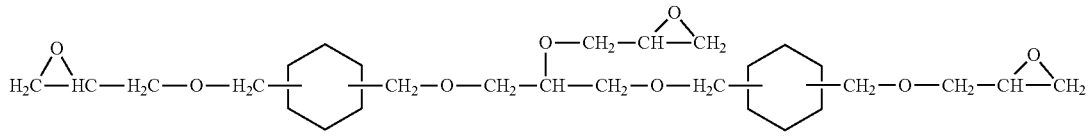

Thus, in the re-epoxidation process of the present invention, the isolated oligomer fraction is subjected to further epoxidation to produce the epoxy resin of the present invention. In this re-epoxidation process, oligomeric components of the PACE resin which are partially epoxidized, that is, they possess free hydroxyl functionality, are further epoxidized. Minor amounts of chlorohydrin intermediates, if any, may also be converted to epoxide functionality.

The epoxy resin composition of the present invention is prepared by a re-epoxidation process comprising reacting Component (I), the PACE resin described above, with (II) an epihalohydrin, and (III) a basic-acting substance, in the presence of (IV) a non-Lewis acid catalyst and, optionally (V) one or more solvents. Component (II) can include any of the epihalohydrins described above with reference to epihalohydrins component (B); Component (III) can include any of the basic-acting substances described above with reference to basic-acting substances component (C); and Component (IV) can include any of the non-Lewis acid catalysts described above, with reference to non-Lewis acid catalysts components (D). Any of the solvents described above with reference to component (E) may also be added to the reaction mixture containing components (I)-(IV).

In the carrying out the process of the present invention, the PACE resin composition useful in the present invention is first produced as a second product stream during the production of a first epoxy resin product stream by epoxidizing an aliphatic or cycloaliphatic hydroxyl containing material, particularly an aliphatic or cycloaliphatic diol such as described herein or in WO2009/142901. After the epoxidation reaction, the PACE resin composition (second epoxy resin product stream) is separated and isolated from the first epoxy resin product stream.

The first and second epoxy products are formed by epoxidizing (i) an aliphatic or cycloaliphatic hydroxyl containing material with (ii) an epihalohydrin, (iii) a basic-acting substance, (iv) a non-Lewis acid catalyst, and optionally, (v) one or more solvents.

With reference to FIG. 1, there is shown a general process for manufacturing an epoxy resin composition of the present invention, the process generally indicated by reference numeral 100. FIG. 1 shows a first series of epoxidation stages, 110, 130, and 150 followed by a washing step after each epoxidation stage including washing stages 120, 140 and 160, respectively. FIG. 1 also shows a second series of epoxidation stages, 180 and, 210 followed by a washing step after each stage including 190 and 220, respectively. It should be understood that the number of epoxidation stages and washing steps used in present invention process may comprise one, two or more stages and the present invention is not limited to the embodiment shown in FIG. 1 which shows three epoxidation stages and three wash steps as a first series and two subsequent epoxidation stages and two wash steps as a second series. In other embodiments, two or more stages or steps of the present invention may be combined and carried out by one apparatus or by two or more separate apparatuses.

With reference to FIG. 1 again, the process 100 includes an aliphatic or cycloaliphatic hydroxyl containing material feed stream 111, an epihalohydrin feed stream 112, a non-Lewis acid catalyst feed stream 113, and a solvent stream 114 along with a basic-acting substance feed stream 115 and an inert gas such as a nitrogen stream 116 are fed into the first epoxidation reaction stage 110 to carry out a first epoxidation reaction. After the first epoxidation reaction, a resultant first epoxidation product, stream 117 from first stage 110, is washed with a water stream 121 at the first washing stage 120 as an aqueous waste stream 122 is directed to a waste recovery operation (not shown) or to another operation for further processing. A washed epoxidation product stream 123 exits from the first washing stage 120.

The washed epoxidation product stream 123 from the first washing stage 120 is forwarded to a second epoxidation stage 130 wherein a second non-Lewis acid catalyst feed stream 130, a second basic-acting substance feed stream 132 and a second inert gas such as a nitrogen stream 133 are fed into the second epoxidation reaction stage 130 to carry out further epoxidation of the washed epoxidation product stream 123 from the first washing stage 120 to form a second epoxidation product stream 134. In an optional embodiment, a second epihalohydrin stream (not shown) and a second solvent stream (not shown) made be fed into the second epoxidation stage 130 if desired. After the second epoxidation reaction, the resultant second epoxidation product, stream 134 from second stage 130, is washed with a water stream 141 at the second washing stage 140 as an aqueous waste stream 142 is directed to a waste recovery operation (not shown) or to another operation for further processing. A washed epoxidation product stream 143 exits from the second washing stage 140.

The washed epoxidation product stream 143 from the second washing stage 140 is forwarded to a third epoxidation stage 150 wherein a third non-Lewis acid catalyst feed stream 151, a third basic-acting substance feed stream 152 and a third inert gas such as a nitrogen stream 153 are fed into the third epoxidation reaction stage 150 to carry out further epoxidation of washed epoxidation product stream 143 from the second washing stage 140 to form a third epoxidation product stream 154. In an optional embodiment, a third epihalohydrin stream (not shown) and a third solvent stream (not shown) made be fed into the second epoxidation stage 150 if desired. After the third epoxidation reaction, the resultant epoxidation product, stream 154 from the third stage 150, is washed with a water stream 161 at the third washing stage 160 as an aqueous waste stream 162 is directed to a waste recovery operation (not shown) or to another operation for further processing. A washed epoxidation product stream 163 exits from the third washing stage 160.

Optionally, in one embodiment, the washed epoxidation product stream 163 from the third washing stage 160 may be forwarded to a devolatilization operation (not shown) to remove any lights (not shown) from the washed epoxidation product 163 to form a crude epoxidation product stream (not shown). In the embodiment shown in FIG. 1, the washed epoxidation product stream 163 is forwarded to a fractionation operation 170 wherein a top lights stream 171, a bottoms stream 172, a partially or partially/fully epoxidized aliphatic or cycloaliphatic hydroxyl containing material stream 173, and a fully epoxidized aliphatic or cycloaliphatic hydroxyl containing material stream 174 are produced. The fully epoxidized aliphatic or cycloaliphatic hydroxyl containing material stream 174 is a purified epoxy resin product which can be used in subsequent processes. The bottoms stream 172 in this embodiment is an example of a polyfunctional aliphatic or cycloaliphatic epoxy (PACE) resin useful in the present invention.

In the present invention, the bottoms stream 172 is forwarded to a second series of epoxidation stages including a fourth epoxidation stage 180 and a fifth epoxidation stage 210. The bottoms stream 172, an epihalohydrin feed stream 181, a fourth non-Lewis acid catalyst feed stream 182, a solvent stream 183, a fourth basic-acting substance feed stream 184, and a fourth inert gas such as a nitrogen stream 185 are fed into the fourth epoxidation reaction stage 180 to carry out further epoxidation of the bottoms stream 172 exiting from the fractionation operation 170 to form a fourth epoxidation product stream 186. After the fourth epoxidation reaction, the resultant epoxidation product, stream 186 from fourth stage 180, is washed with a water stream 191 at the fourth washing stage 190 as an aqueous waste stream 192 is directed to a waste recovery operation (not shown) or to another operation for further processing. A washed epoxidation product stream 193 exits from the fourth washing stage 190.

The washed epoxidation product stream 193 from the fourth washing stage 190 is forwarded to a fifth epoxidation stage 210 wherein a fifth non-Lewis acid catalyst feed stream 211, a fifth basic-acting substance feed stream 212 and a fifth inert gas such as a nitrogen stream 213 are fed into the fifth epoxidation reaction stage 210 to carry out further epoxidation of the washed epoxidation product stream 193 from the fourth washing stage 190 to form a fifth epoxidation product stream 214. In an optional embodiment, an epihalohydrin stream (not shown) and a solvent stream (not shown) made be fed into the fifth epoxidation stage 210 if desired. After the fifth epoxidation reaction, the resultant epoxidation product, stream 214 from the fifth stage 210, is washed with a water stream 221 at a fifth washing stage 220 as an aqueous waste stream 222 is directed to a waste recovery operation (not shown) or to another operation for further processing. A washed epoxidation product stream 223 exits from the fifth washing stage 210.

The washed epoxidation product stream 223 from the fifth washing stage 220 is forwarded to a devolatilization operation 230 to remove any lights 231 from the washed epoxidation product and to form a re-epoxidized product stream 232. Although not shown, in one embodiment, the re-epoxidation product stream 232 may be forwarded to a blending operation to be blended with a curing agent stream to form a curable composition. The resultant curable composition may subsequently be cured to form a thermoset. Optionally, any other additive stream, for example an epoxy resin other than the re-epoxidized PACE resin, may be blended with the epoxidation product stream 232 and curing agent stream to form the curable composition.

It should be understood that any conventional equipment known to those skilled artisans can be used to carry out the manufacturing process of the present invention. For example, the equipment can include epoxidation reactor vessels; evaporation vessels such as rotary evaporators; and separation vessels such as distillation apparatus; which are known in the art. For example, generally, a separation vessel, such as a fractional vacuum distillation apparatus 170 may be used to produce several fractionation cuts including a "lights" stream 171, a "bottoms" stream 172 comprising unrecovered fully epoxidized aliphatic or cycloaliphatic hydroxyl containing material and oligomers, a stream of partially or partially/fully epoxidized aliphatic or cycloaliphatic hydroxyl containing mixtures 173, and a stream of high purity fully epoxidized aliphatic or cycloaliphatic hydroxyl containing material product 174. The bottoms stream 172 is separated and isolated from the other streams leaving the distillation apparatus. The high purity fully epoxidized aliphatic or cycloaliphatic hydroxyl containing material product stream shown in FIG. 1 as stream 174 may be forwarded to a subsequent process to form curable compositions and thermosets therefrom. In one embodiment, the bottoms stream 172 may also be forwarded to a subsequent process to form curable compositions and thermosets therefrom. In the embodiment shown in FIG. 1, the bottoms stream 172 is re-epoxidized by the process and equipment described above to form the re-epoxidized product stream 232 of the present invention.

Another embodiment of the present invention concerns a thermosettable (curable) epoxy resin composition comprising (A) a polyfunctional aliphatic and/or cycloaliphatic epoxy resin composition prepared by re-epoxidizing oligomeric products present in an oligomer fraction separated and isolated from an epoxy resin formed by the epoxidation of an aliphatic or cycloaliphatic hydroxyl containing material using (1) a basic-acting substance, (2) non-Lewis acid catalyst, and (3) an epihalohydrin, and optionally, (4) one or more solvents; (B) an epoxy resin curing agent and/or an epoxy resin curing catalyst; and (C) optionally, an epoxy resin compound other than the re-epoxidized PACE resin (A).

The term "curable" (also referred to as "thermosettable") means that the composition is capable of being subjected to conditions which will render the composition to a cured or thermoset state or condition. The term "cured" or "thermoset" is defined by L. R. Whittington in *Whittington's Dictionary of Plastics* (1968) on page 239 as follows: "Resin or plastics compounds which in their final state as finished articles are substantially infusible and insoluble. Thermosetting resins are often liquid at some stage in their manufacture or processing, which are cured by heat, catalysis, or some other chemical means. After being fully cured, thermosets cannot be resoftened by heat. Some plastics which are normally thermoplastic can be made thermosetting by means of crosslinking with other materials."

The thermosettable epoxy resin composition of the present invention is prepared by admixing (a) the re-epoxidized PACE resin composition of the present invention, with (b) an epoxy resin curing agent and/or a curing catalyst; and (c) optionally, an epoxy resin other than the re-epoxidized PACE resin composition (a) of the present invention. The curing agent and/or curing catalyst are used in amounts which will effectively thermoset the curable epoxy resin composition, with the understanding that the amounts will depend upon the specific re-epoxidized PACE resin, any optionally used epoxy resin, and the curing agent and/or catalyst employed.

Generally, the ratio of the curing agent and the re-epoxidized PACE resin and epoxy resin other than the re-epoxidized PACE resin if used is from about 0.60:1 to about 1.50:1, and preferably from about 0.95:1 to about 1.05:1 equivalents of reactive hydrogen atom present in the curing agent per equivalent of epoxide group in the epoxy resin(s) at the conditions employed for curing.

A preferred curable epoxy resin composition of the present invention comprises an aliphatic and/or cycloaliphatic curing agent and the re-epoxidized PACE resin. The curable epoxy resin composition, when cured, provides a cured epoxy resin free of any aromatic group.

A more specific preferred curable epoxy resin composition of the present invention comprises an alkyleneamine (polyalkylenepolyamine) curing agent, such as, for example, ethylenediamine, diethylenetriamine or triethylenetetramine and the re-epoxidized PACE resin. The curable epoxy resin composition, when cured, provides a cured epoxy resin free of any aromatic group.

Another preferred curable epoxy resin composition of the present invention comprises the (1) aliphatic and/or cycloaliphatic curing agent, (2) the re-epoxidized PACE resin and (3) an epoxy resin other than the PACE resin wherein the epoxy resin (3) comprises one or more of aliphatic and/or cycloaliphatic epoxy resins. The curable epoxy resin composition, when cured, provides a cured epoxy resin free of any aromatic group.

A more specific preferred curable epoxy resin composition of the present invention comprises (1) an alkyleneamine (polyalkylenepolyamine) curing agent, (2) the re-epoxidized PACE resin and (3) an epoxy resin other than the re-epoxidized PACE resin wherein the epoxy resin (3) comprises one or more of aliphatic and/or cycloaliphatic epoxy resins. The curable epoxy resin composition, when cured, provides a cured epoxy resin free of any aromatic group.

The epoxy resin curing agent and/or curing catalyst used in the present invention to form the thermosettable mixture with the re-epoxidized PACE resin comprises at least one material having two or more reactive hydrogen atoms per molecule. The reactive hydrogen atoms are reactive with epoxide groups, such as those epoxide groups contained in the re-epoxidized PACE resin.

Certain of the hydrogen atoms can be non-reactive with the epoxide groups in the initial process of forming the cured product but reactive in a later process of curing the epoxy resin, when there are other functional groups, which are much more reactive with the epoxide groups under reaction conditions used, present in the B-staging or thermosetting reaction of forming the thermoset product. For example, a reactive compound may have two different functional groups each bearing at least one reactive hydrogen atom, with one functional group being inherently more reactive with an epoxide group than the other under the reaction conditions used. These reaction conditions may include the use of a catalyst which favors a reaction of the reactive hydrogen atom(s) of one functional group with an epoxide group over a reaction of the reactive hydrogen atom(s) of the other functional group with an epoxide group. The catalyst may also be latent, for example under conditions of mixing the thermosettable mixture, then activated at a later time, for example by heating of the latently catalyzed thermosettable mixture.

Other non-reactive hydrogen atoms may also include hydrogen atoms in the secondary hydroxyl groups which form during an epoxide ring opening reaction in the process of producing the partially cured or fully cured product.

The curing agent may further comprise aliphatic, cycloaliphatic and/or aromatic groups within the curing agent structure. The aliphatic groups may be branched or unbranched. The aliphatic or cycloaliphatic groups may also be saturated or unsaturated and may comprise one or more substituents which are inert (not reactive) to the process of preparing the thermosettable compositions and thermosets of the present invention. The substituents may be attached to a terminal carbon atom or may be between two carbon atoms, depending on the chemical structures of the substituents. Examples of such inert substituents include halogen atoms, preferably chlorine or bromine, nitrile, nitro, alkyloxy, keto, ether (—O—), thioether (—S—), or tertiary amine. The aromatic ring, if present within the curing agent structure, may comprise one or more heteroatoms such as N, O, S and the like.

Examples of the curing agent may include compounds such as (a) di- and polyphenols, (b) di- and polycarboxylic acids, (c) di- and polymercaptans, (d) di- and polyamines, (e) primary monoamines, (f) sulfonamides, (g) aminophenols, (h) aminocarboxylic acids, (i) phenolic hydroxyl containing carboxylic acids, (j) sulfanilamides, and (k) any combination of any two or more of such compounds or the like.

Examples of the di- and polyphenols (a) include 1,2-dihydroxybenzene (catechol); 1,3-dihydroxybenzene (resorcinol); 1,4-dihydroxybenzene (hydroquinone); 4,4'-isopropylidenediphenol (bisphenol A); 4,4'-dihydroxydiphenylmethane; 3,3',5,5'-tetrabromobisphenol A; 4,4'-thiodiphenol; 4,4'-sulfonyldiphenol; 2,2'-sulfonyl-4,4'-dihydroxydiphenyl oxide; 4,4'-dihydroxybenzophenone; 1,1'-bis(4-hydroxyphenyl)-1-phenylethane; 3,3', 5,5'-tetrachlorobisphenol A; 3,3'-dimethoxybisphenol A; 3,3',5,5'-tetramethyl-4,4'-dihydroxydiphenyl; 4,4'-dihydroxybiphenyl; 4,4'-dihydroxy-alpha-methylstilbene; 4,4'-dihydroxybenzanilide; 4,4'-dihydroxystilbene; 4,4'-dihydroxy-alpha-cyanostilbene; 1,1-bis(4-hydroxyphenyl) cyclohexane; 1,4-dihydroxy-3,6-dimethylbenzene; 1,4-dihydroxy-3,6-dimethoxybenzene; 1,4-dihydroxy-2-tert-butylbenzene; 1,4-dihydroxy-2-bromo-5-methylbenzene; 1,3-dihydroxy-4-nitrophenol; 1,3-dihydroxy-4-cyanophenol; tris(hydroxyphenyl)methane, dicyclopentadiene or an oligomer thereof and phenol or substituted phenol condensation products, and any mixture thereof.

Examples of the di- and polycarboxylic acids (b) include terephthalic acid, isophthalic acid, dicyclopentadienedicarboxylic acid, tris(carboxyphenyl)methane, 4,4'-dicarboxydiphenylmethane; 1,4-cyclohexanedicarboxylic acid; 1,6-hexanedicarboxylic acid; 1,4-butanedicarboxylic acid; 1,1-bis(4-carboxyphenyl)cyclohexane; 3,3',5,5'-tetra-methyl-4, 4'-dicarboxydiphenyl; 4,4'-dicarboxy-alpha-methylstilbene; 1,4-bis(4-carboxy-phenyl)-trans-cyclohexane; 1,1'-bis(4-carboxyphenyl)cyclohexane; 1,3-dicarboxy-4-methylbenzene; 1,3-dicarboxy-4-methoxybenzene; 1,3-dicarboxy-4-bromobenzene; and any combination thereof.

Examples of the di- and polymercaptans (c) include 1,3-benzenedithiol; 1,4-benzenedithiol; 4,4'-dimercaptodiphenylmethane; 4,4'-dimercaptodiphenyl oxide; 4,4'-dimercapto-alpha-methylstilbene; 3,3',5,5'-tetramethyl-4,4'-dimercaptodiphenyl; 1,4-cyclohexanedithiol; 1,6-hexanedithiol; 2,2'-dimercaptodiethylether; 1,1-bis(4-mercapto-phenyl)cyclohexane; 1,2-dimercaptopropane, bis (2-mercaptoethyl)sulfide, tris(mercapto-phenyl)methane, and any combination thereof.

Examples of the di- and polyamines (d) include 1,2-diaminobenzene; 1,3-diaminobenzene; 1,4-diaminobenzene; 4,4'-diaminodiphenylmethane; 4,4'-diaminodiphenylsulfone; 2,2'-diaminodiphenylsulfone; 4,4'-diaminodiphenyl oxide; 3,3',5,5'-tetramethyl-4,4'-diaminodiphenyl; 3,3'-dimethyl-4, 4'-diaminodiphenyl; 4,4'-diamino-alpha-methylstilbene; 4,4'-diaminobenzanilide; 4,4'-diaminostilbene; 1,4-bis(4-aminophenyl)-trans-cyclohexane; 1,1-bis(4-aminophenyl) cyclohexane; 1,2-cyclohexanediamine; 1,4-bis(aminocyclohexyl)methane; 1,3-bis(aminomethyl)cyclohexane; 1,4-bis (aminomethyl)cyclohexane; 1,4-cyclohexanediamine; 1,6-hexanediamine; 2,2'-bis(4-aminocyclohexyl)propane; 4-(2-aminopropan-2-yl)-1-methylcyclohexan-1-amine (menthane diamine); piperazine, ethylenediamine, diethyletriamine, triethylenetetramine, tetraethylenepentamine, 1-(2-aminoethyl)piperazine, bis(aminopropyl)ether, bis(aminopropyl)sulfide, bis(aminomethyl)norbornane, isophoronediamine, 1,3-xylenediamine, tris(aminophenyl)methane, and any combination thereof.

Examples of the primary monoamines (e) include ammonia, aniline, 4-chloroaniline, 4-methylaniline, 4-methoxyaniline, 4-cyanoaniline, 4-aminodiphenyl oxide, 4-aminodiphenylmethane, 4-aminodiphenylsulfide, 4-aminobenzophenone, 4-aminodiphenyl, 4-aminostilbene, 4-amino-alpha-methylstilbene, methylamine, 4-amino-4'-nitrostilbene, n-hexylamine, cyclohexylamine, aminonorbornane, N,N-diethyltrimethylenediamine; 2,6-dimethylaniline; and any combination thereof.

Examples of the sulfonamides (f) include phenylsulfonamide, 4-methoxyphenylsulfonamide, 4-chlorophenylsulfonamide, 4-bromophenylsulfonamide, 4-methylsulfonamide, 4-cyanosulfonamide, 4-sulfonamidodiphenyl oxide, 4-sulfonamidodiphenylmethane, 4-sulfonamidobenzophenone, 4-sulfonylamidodiphenyl, 4-sulfonamidostilbene, 4-sulfonamido-alpha-methylstilbene, 2,6-dimethyphenylsulfonamide; and any combination thereof.

Examples of the aminophenols (g) include o-aminophenol, m-aminophenol, p-aminophenol, 2-methoxy-4-hydroxyaniline, 3-cyclohexyl-4-hydroxyaniline, 5-butyl-4-hydroxyaniline, 3-phenyl-4-hydroxyaniline, 4-(1-(3-aminophenyl)-1-methyl-ethyl)phenol, 4-(1-(4-aminophenyl)ethyl)phenol, 4-(4-aminophenoxy)phenol, 4-((4-amino-phenyl)thio)phenol, (4-aminophenyl)(4-hydroxyphenyl)methanone, 4-((4-amino-phenyl)sulfonyl)phenol, N-methyl-p-aminophenol, 4-amino-4'-hydroxy-alpha-methyl-stilbene, 4-hydroxy-4'-amino-alpha-methylstilbene, 4-(1-(4-amino-3,5-dibromophenyl)-1-methylethyl)-2,6-dibromophenol; 3,5-dimethyl-4-hydroxyaniline; 2,6-dibromo-4-hydroxy-aniline; and any combination thereof.

Examples of the aminocarboxylic acids (h) include 2-aminobenzoic acid, 3-aminobenzoic acid, 4-aminobenzoic acid, 2-methoxy-4-aminobenzoic acid, 3-cyclohexyl-4-aminobenzoic acid, 5-butyl-4-aminobenzoic acid, 3-phenyl-4-aminobenzoic acid, 4-(1-(3-aminophenyl)-1-methylethyl)benzoic acid, 4-(1-(4-aminophenyl)ethyl)benzoic acid, 4-(4-aminophenoxy)benzoic acid, 4-((4-aminophenyl)thio) benzoic acid, (4-aminophenyl)(4-carboxyphenyl) methanone, 4-((4-aminophenyl)sulfonyl)benzoic acid, N-methyl-4-aminobenzoic acid, 4-amino-4'-carboxy-alpha-methylstilbene, 4-carboxy-4'-amino-alpha-methylstilbene, glycine, N-methylglycine, 4-aminocyclohexanecarboxylic acid, 4-aminohexanoic acid, 4-piperidinecarboxylic acid, 5-aminophthalic acid, 4-(1-(4-amino-3,5-dibromophenyl)-1-methylethyl)-2,6-dibromobenzoic acid; 3,5-dimethyl-4-aminobenzoic acid; 2,6-dibromo-4-aminobenzoic acid; and any combination thereof.

Examples of the carboxylic acids (i) include 2-hydroxybenzoic acid, 3-hydroxybenzoic acid, 4-hydroxybenzoic acid, 2-methoxy-4-hydroxybenzoic acid, 3-cyclohexyl-4-hydroxybenzoic acid, 5-butyl-4-hydroxybenzoic acid, 3-phenyl-4-hydroxybenzoic acid, 4-(1-(3-hydroxyphenyl)-1-methylethyl)benzoic acid, 4-(1-(4-hydroxyphenyl)ethyl) benzoic acid, 4-(4-hydroxyphenoxy)benzoic acid, 4-((4-hydroxyphenyl)thio)benzoic acid, (4-hydroxyphenyl)(4-carboxyphenyl)methanone, 4-((4-hydroxyphenyl)sulfonyl) benzoic acid, 4-hydroxy-4'-carboxy-alpha-methylstilbene, 4-carboxy-4'-hydroxy-alpha-methylstilbene, 2-hydroxyphenylacetic acid, 3-hydroxyphenylacetic acid, 4-hydroxyphenylacetic acid, 4-hydroxyphenyl-2-cyclo-hexanecarboxylic acid, 4-hydroxyphenoxy-2-propanoic acid, 3,5-dimethyl-4-hydroxybenzoic acid; 2,6-dibromo-4-hydroxybenzoic acid; 4-(1-(4-hydroxy-3,5-dibromophenyl)-1-methylethyl)-2,6-dibromobenzoic acid; and any combination thereof.

Examples of the sulfanilamides (j) include o-sulfanilamide, m-sulfanilamide, p-sulfanilamide, 2-methoxy-4-aminobenzoic acid, 3-methyl-4-sulfonamido-1-aminobenzene, 5-methyl-3-sulfonamido-1-aminobenzene, 3-phenyl-4-sulfonamido-1-aminobenzene, 4-(1-(3-sulfonamidophenyl)-1-methylethyl)aniline, 4-(1-(4-sulfonamidophenyl)ethyl) aniline, 4-(4-sulfonamidophenoxy)aniline, 4-((4-sulfonamidophenyl)thio)aniline, (4-sulfonamidophenyl)(4-aminophenyl)methanone, 4-((4-sulfonamidophenyl) sulfonyl)aniline, 4-sulfonamido-1-N-methylaminobenzene, 4-amino-4'-sulfonamido-alpha-methylstilbene, 4-sulfonamido-4'-amino-alpha-methyl-stilbene, 2,6-dimethyl-4-sulfonamido-1-aminobenzene; 4-(1-(4-sulfonamido-3,5-dibromo-phenyl)-1-methylethyl)-2,6-dibromoaniline; and any combination thereof.

Particularly preferred examples of the curing catalyst include boron trifluoride, boron trifluoride etherate, aluminum chloride, ferric chloride, zinc chloride, silicon tetrachloride, stannic chloride, titanium tetrachloride, antimony trichloride, boron trifluoride monoethanolamine complex, boron trifluoride triethanolamine complex, boron trifluoride piperidine complex, pyridine-borane complex, diethanolamine borate, zinc fluoroborate, metallic acylates such as stannous octoate or zinc octoate, and any combination thereof.

The curing catalyst may be employed in an amount which will effectively thermoset the curable epoxy resin composition or assist in the thermosetting of the thermosettable epoxy resin composition. The amount of the curing catalyst will also depend upon the particular re-epoxidized PACE resin, the curing agent, if any, and epoxy resin other than the PACE resin, if any, employed in the thermosettable epoxy resin composition.

Generally, the curing catalyst may be used in an amount of from about 0.001 wt % to about 2 wt %, based on the weight of the total thermosettable epoxy resin composition. In addition, one or more of the curing catalysts may be employed to accelerate or otherwise modify the curing process of the curable epoxy resin composition.

The epoxy resin which can optionally be used as the epoxy resin (c) other than the re-epoxidized PACE resin (a) may be any epoxide containing compound which has an average of more than one epoxide group per molecule. The epoxide group can be attached to any oxygen, sulfur or nitrogen atom or the single bonded oxygen atom attached to the carbon atom of a —CO—O— group. The oxygen, sulfur, nitrogen atom, or the carbon atom of the —CO—O— group may be attached to an aliphatic, cycloaliphatic, polycycloaliphatic or aromatic hydrocarbon group. The aliphatic, cycloaliphatic, polycycloaliphatic or aromatic hydrocarbon group can be substituted with any inert substituents including, but not limited to, halogen atoms, preferably fluorine, bromine or chlorine; nitro groups; or the groups can be attached to the terminal carbon atoms of a compound containing an average of more than one —(O—CHR$^a$—CHR$^a$)$_t$— group, wherein each R$^a$ is independently a hydrogen atom or an alkyl or haloalkyl group containing from one to two carbon atoms, with the proviso that only one R$^a$ group can be a haloalkyl group, and t has a value from one to about 100, preferably from one to about 20, more preferably from one to about 10, and most preferably from one to about 5.

More specific examples of the epoxy resin which can be used as the epoxy resin (c) include diglycidyl ethers of 1,2-dihydroxybenzene (catechol); 1,3-dihydroxybenzene (resorcinol); 1,4-dihydroxybenzene (hydroquinone); 4,4'-isopropylidenediphenol (bisphenol A); 4,4'-dihydroxydiphenylmethane; 3,3',5,5'-tetrabromobisphenol A; 4,4'-thiodiphenol; 4,4'-sulfonyldiphenol; 2,2'-sulfonyldiphenol; 4,4'-dihydroxydiphenyl oxide; 4,4'-dihydroxybenzophenone; 1,1'-bis(4-hydroxyphenyl)-1-phenylethane; 3,3'-5,5'-tetrachlorobisphenol A; 3,3'-dimethoxybisphenol A; 4,4'-dihydroxybiphenyl; 4,4'-dihydroxy-alpha-methylstilbene; 4,4'-dihydroxybenzanilide; 4,4'-dihydroxystilbene; 4,4'-dihydroxy-alpha-cyanostilbene; N,N'-bis(4-hydroxyphenyl)terephthalamide; 4,4'-dihydroxyazobenzene; 4,4'-dihydroxy-2,2'-dimethylazoxybenzene; 4,4'-dihydroxydiphenylacetylene; 4,4'-dihydroxychalcone; the tetraglycidyl amines of 4,4'-diaminodiphenylmethane; 4,4'-diaminostilbene; N,N'-dimethyl-4,4'-diaminostilbene; 4,4'-diaminobenzanilide; 4,4'-diaminobiphenyl; 4-hydroxyphenyl-4-hydroxybenzoate, dipropylene glycol, poly(propylene glycol), thiodiglycol, the triglycidyl ether of tris(hydroxyphenyl) methane, the polyglycidyl ethers of a phenol or alkyl or halogen substituted phenol-aldehyde acid catalyzed condensation product (novolac resins), the polyglycidyl ether of the condensation product of a dicyclopentadiene or an oligomer thereof and a phenol or alkyl or halogen substituted phenol, and any combination thereof.

The epoxy resin which can be used as the epoxy resin may also include an advanced epoxy resin product. The advanced epoxy resin may be a product of an advancement reaction of an epoxy resin with an aromatic di- and polyhydroxyl, or carboxylic acid containing compound. The epoxy resin used in the advancement reaction may include any one or more of the aforesaid epoxy resins suitable for the epoxy resin comprising the di- or polyglycidyl ethers.

Examples of the aromatic di- and polyhydroxyl or carboxylic acid containing compound include 4,4'-dihydroxydiphenylmethane; 4,4'-thiodiphenol; 4,4'-sulfonyldiphenol; 2,4-dimethylresorcinol; 2,2'-sulfonyldiphenol; 4,4'-dihydroxydiphenyl oxide; 4,4'-dihydroxybenzophenone; 1,1-bis(4-hydroxyphenyl)-1-phenylethane; 4,4'-bis(4(4-hydroxyphenoxy)-phenylsulfone)diphenyl ether; 4,4'-dihydroxydiphenyl disulfide; 3,3',3,5'-tetrachloro-4,4'-isopropylidenediphenol; 3,3',3,5'-tetrabromo-4,4'-isopropylidenediphenol; 3,3'-dimethoxy-4,4'-isopropylidene-diphenol; 4,4'-dihydroxybiphenyl; 4,4'-dihydroxy-alpha-methylstilbene; 4,4'-dihydroxybenzanilide; bis(4-hydroxyphenyl)terephthalate; N,N'-bis(4-hydroxyphenyl)terephthalamide; 4,4'-dihydroxyphenylbenzoate; bis(4'-hydroxyphenyl)-1,4-benzenediimine; 1,1'-bis(4-hydroxyphenyl)cyclohexane; 2,2',5,5'-tetrahydroxydiphenylsulfone; bis(4'-hydroxybiphenyl) terephthalate; 4,4'-benzanilidedicarboxylic acid; 4,4'-phenylbenzoatedicarboxylic acid; 4,4'-stilbenedicarboxylic acid, hydroquinone, resorcinol, catechol, 4-chlororesorcinol, tetramethylhydroquinone, bisphenol A, phloroglucinol, pyrogallol,tris(hydroxyphenyl)methane, dicyclopentadiene diphenol, tricyclopentadienediphenol, terephthalic acid, isophthalic acid, adipic acid, and any combination thereof.

Preparation of the aforementioned advanced epoxy resin products can be performed using known methods, for example, an advancement reaction of an epoxy resin with one or more suitable compounds having an average of more than one reactive hydrogen atom per molecule, wherein the reactive hydrogen atom is reactive with an epoxide group in the epoxy resin.

The ratio of the compound having an average of more than one reactive hydrogen atom per molecule to the epoxy resin is generally from about 0.01:1 to about 0.95:1, preferably from about 0.05:1 to about 0.8:1, and more preferably from about 0.10:1 to about 0.5:1 equivalents of the reactive hydrogen atom per equivalent of the epoxide group in the epoxy resin.

In addition to the aforementioned dihydroxyaromatic and dicarboxylic acid compounds, examples of the compound having an average of more than one reactive hydrogen atom per molecule may also include dithiol, disulfonamide or compounds containing one primary amine or amide group, two secondary amine groups, one secondary amine group and one phenolic hydroxy group, one secondary amine group and one carboxylic acid group, or one phenolic hydroxy group and one carboxylic acid group, and any combination thereof.

The advancement reaction may be conducted in the presence or absence of a solvent with the application of heat and mixing. The advancement reaction may be conducted at atmospheric, superatmospheric or subatmospheric pressures and at temperatures of from about 20° C. to about 260° C., preferably, from about 80° C. to about 240° C., and more preferably from about 100° C. to about 200° C.

The time required to complete the advancement reaction depends upon factors such as the temperature employed, the chemical structure of the compound having more than one reactive hydrogen atom per molecule employed, and the chemical structure of the epoxy resin employed. Higher temperature may require shorter reaction time whereas lower temperature requires a longer period of reaction time. In general, the time for completion of the advancement reaction may ranged from about 5 minutes to about 24 hours, preferably from about 30 minutes to about 8 hours, and more preferably from about 30 minutes to about 4 hours.

A catalyst may also be added in the advancement reaction. Examples of the catalyst may include phosphines, quaternary ammonium compounds, phosphonium compounds and tertiary amines. The catalyst may be employed in quantities of from about 0.01 wt % to about 3 wt %, preferably from about 0.03 wt % to about 1.5 wt %, and more preferably from about 0.05 wt % to about 1.5 wt %, based upon the total weight of the epoxy resin.

Other details concerning an advancement reaction useful in preparing the advanced epoxy resin product for the resin are provided in U.S. Pat. No. 5,736,620 and in *Handbook of Epoxy Resins* by Henry Lee and Kris Neville, both of which are incorporated herein by reference.

The thermosettable epoxy resin composition may also be blended with at least one additive including, for example, a cure accelerator, a solvent or diluent, a modifier such as a flow modifier and/or a thickener, a reinforcing agent, a filler, a pigment, a dye, a mold release agent, a wetting agent, a stabilizer, a fire retardant agent, a surfactant, or any combination thereof.

The additive may be blended with the re-epoxidized PACE resin, the curing agent, if used, and the epoxy resin other than the re-epoxidized PACE resin, if used or with any combination thereof prior to use for the preparation of the thermosettable epoxy resin composition of the present invention.

These additives may be added in functionally equivalent amounts, for example, the pigment and/or dye may be added in quantities which will provide the composition with the desired color. In general, the amount of the additives may be from about zero wt % to about 20 wt %, preferably from about 0.5 wt % to about 5 wt %, and more preferably from about 0.5 wt % to about 3 wt %, based upon the total weight of the thermosettable epoxy resin composition.

The cure accelerator which can be employed herein includes, for example, mono, di, tri and tetraphenols; chlorinated phenols; aliphatic or cycloaliphatic mono or dicarboxylic acids; aromatic carboxylic acids; hydroxybenzoic acids; halogenated salicylic acids; boric acid; aromatic sulfonic acids; imidazoles; tertiary amines; aminoalcohols; aminopyridines; aminophenols; mercaptophenols; and any mixture thereof.

Particularly suitable cure accelerators include 2,4-dimethylphenol, 2,6-dimethylphenol, 4-methylphenol, 4-tertiarybutylphenol, 2-chlorophenol, 4-chlorophenol, 2,4-dichlorophenol, 4-nitrophenol, 1,2-dihydroxybenzene, 1,3-dihydroxybenzene, 2,2'-dihydroxybiphenyl, 4,4'-isopropylidenediphenol, valeric acid, oxalic acid, benzoic acid, 2,4-dichlorobenzoic acid, 5-chlorosalicylic acid, salicylic acid, p-toluenesulfonic acid, benzenesulfonic acid, hydroxybenzoic acid, 4-ethyl-2-methylimidazole, 1-methylimidazole, triethylamine, tributylamine, N,N-diethylethanolamine, N,N-dimethylbenzylamine, 2,4,6-tris(dimethylamino)phenol, 4-dimethylaminopyridine, 4-aminophenol, 2-aminophenol, 4-mercaptophenol, and any combination thereof.

Examples of the solvent or diluent which can be employed herein include, for example, aliphatic and aromatic hydrocarbons, halogenated aliphatic hydrocarbons, aliphatic ethers, aliphatic nitriles, cyclic ethers, glycol ethers, esters, ketones, amides, sulfoxides, and any combination thereof.

Particularly suitable solvents include pentane, hexane, octane, toluene, xylene, methylethylketone, methylisobutylketone, N,N-dimethylformamide, dimethylsulfoxide, diethyl ether, tetrahydrofuran, 1,4-dioxane, dichloromethane, chloroform, ethylene dichloride, methyl chloroform, ethylene glycol dimethyl ether, diethylene glycol methyl ether, dipropylene glycol methyl ether, N-methylpyrrolidinone, N,N-dimethylacetamide, acetonitrile, sulfolane, and any combination thereof.

The modifier such as the thickener and the flow modifier may be employed in amounts of from zero wt % to about 10 wt %, preferably, from about 0.5 wt % to about 6 wt %, and more preferably from about 0.5 wt % to about 4 wt %, based upon the total weight of the thermosettable epoxy resin blend composition.

The reinforcing material which may be employed herein includes natural and synthetic fibers in the form of woven fabric, mat, monofilament, multifilament, unidirectional fiber, roving, random fiber or filament, inorganic filler or whisker, or hollow sphere. Other suitable reinforcing material includes glass, carbon, ceramics, nylon, rayon, cotton, aramid, graphite, polyalkylene terephthalates, polyethylene, polypropylene, polyesters, and any combination thereof.

The filler which may be employed herein includes, for example, inorganic oxide, ceramic microsphere, plastic microsphere, glass microsphere, inorganic whisker, calcium carbonate, and any combination thereof.

The filler may be employed in an amount of from zero wt % to about 95 wt %, preferably from about 10 wt % to about 80 wt %, and more preferably from about 40 wt % to about 60 wt %, based upon the total weight of the thermosettable epoxy resin composition.

Another embodiment of the present invention comprises a partially (B-staged) or a totally cured (thermoset) product from the thermosettable epoxy resin composition described above.

The process of thermosetting the thermosettable epoxy resin composition of the present invention may be conducted at atmospheric (e.g. 760 mm Hg), superatmospheric or subatmospheric pressures and at a temperature from about 0° C. to about 300° C., preferably from about 25° C. to about 250° C., and more preferably from about 50° C. to about 200° C.

The time required to complete the curing may depend upon the temperature employed. Higher temperatures generally require a shorter period of time whereas lower temperatures generally require longer periods of time. In general, the required time for completion of the curing is from about 1 minute to about 48 hours, preferably from about 15 minutes to about 24 hours, and more preferably from about 30 minutes to about 12 hours. It is also operable to partially thermoset the thermosettable epoxy resin composition of the present invention to form a B-stage product and subsequently cure the B-stage product completely at a later time.

Another embodiment of the present invention comprises an article prepared from the B-staged (partially thermoset) or the totally cured (thermoset) product described above. The article may include, for example, coatings, especially protective coatings with excellent solvent resistant, moisture resistant, abrasion resistant, impact resistant, and weatherable (e.g., UV resistant, non-chalking) properties; a reactive toughener for thermosets including epoxy resin based thermosets; can and coil coatings; maintenance coatings including coatings for stone, concrete and flooring; marine coatings including anti-fouling coatings; powder coatings including both decorative and functional types; automotive coatings; corrosion resistant coatings; electrical or structural laminates and composites; encapsulations; general castings; coatings for other plastics and metals; sealants; filament windings; moldings; polymer modified concrete; binders; adhesives including window glass adhesives; paints lacquers, and varnishes. Articles which comprise a fully aliphatic/cycloaliphatic cured epoxy resin (with no aromatic rings) of the present invention are especially desirable for their outstanding balance of physical and mechanical properties.

EXAMPLES

The following Examples and Comparative Examples further illustrate the present invention in detail but are not to be construed to limit the scope thereof.

The following standard abbreviations are used in the Examples and Comparative Examples: "GC" stands for gas chromatography (chromatographic); "MS" stands for mass spectrometry (spectrometric); "DSC" stands for differential scanning calorimetry; "Tg" stands for glass transition temperature(s); "EEW" stands for epoxide equivalent weight; "AHEW" stands for amine hydrogen equivalent weight; "DI" stands for deionized; "meq" stands for milliequivalent(s); "eq" stands for equivalent(s); "wt" stands for weight(s); "min" stands for minute(s); "hr" stands for hour(s); "g" stands for gram(s); "mL" stands for milliliter(s); "L" stands for liter(s); "LPM" stands for liter(s) per minute; "am" stands for micrometer(s); "mm" stands for millimeter(s); "m" stands for meter(s); "cp" stands for centipoise; "J" stands for joule(s); and "DETA" stands for diethylenetriamine.

In the following Examples and Comparative Examples, standard analytical equipment and methods are used such as for example, the following:

Gas Chromatogaphic Analysis: Area %

In the general method, a Hewlett Packard 5890 Series II Plus gas chromatograph was employed using a DB-1 capillary column (61.4 m by 0.25 mm with a 0.25 μm film thickness, Agilent). The column was maintained in the chromatograph oven at a 50° C. initial temperature. Both the injector inlet and flame ionization detector were maintained at 300° C. Helium carrier gas flow through the column was maintained at 1.1 mL per min. For the analyses of the epoxy resins during synthesis or from the rotary evaporation, an initial 50° C. oven temperature with heating at 12° C. per min to a final temperature of 300° C. revealed that essentially all light boiling components, including residual epichlorohydrin, cyclohexanedimethanols and monoglycidyl ethers of the cyclohexanedimethanols had been removed by the rotary evaporation. For the analyses of the PACE resins and re-epoxidized PACE resins, an initial 250° C. oven temperature with heating at 13.3° C. per min to a final temperature of 300° C. was employed for complete elution of all oligomeric components within 50 min total time for the analysis. GC analyses in area %, are not a quantitative measure of any given component.

Samples for GC analysis were prepared by collection of a 0.5 mL aliquot of the slurry product from the epoxidation and addition to a vial containing 1 mL of acetonitrile. After shaking to mix, a portion of the slurry in acetonitrile was loaded into a 1 mL syringe (Norm-Ject, all polypropylene/polyethylene, Henke Sass Wolf GmBH) and passed through a syringe filter (Acrodisc CR 13 with 0.2 μm PTFE membrane, Pall Corporation, Gelman Laboratories) to remove any insoluble debris.

Internally Standardized Gas Chromatographic Analysis for Weight Percent Residual Diglycidyl Ethers of Cis-, Trans-1,3- and 1,4-Cyclohexanedimethanol in the Polyfunctional Cycloaliphatic Epoxy Resin and Re-Epoxidized Polyfunctional Cycloaliphatic Epoxy Resin A single point internal standard method was developed for gas chromatographic analysis of residual diglycidyl ethers of cis-, trans-1,3- and 1,4-cyclohexanedimethanol remaining in the PACE resin (distillation pot) product and the re-epoxidized PACE resin. Cyclohexanone was selected as the internal standard since it had a retention time that was different from that of any other components observed in the analyses of the epoxidation products. For the standard of the diglycidyl ether of cis-, trans-1,3- and 1,4-cyclohexanedimethanol, a distillation cut was employed. This distillation cut contained 0.71 wt % monoglycidyl ethers and 99.29 wt % diglycidyl ethers. A 0.2500 g sample of the standard of the diglycidyl ethers plus 0.7500 g of acetonitrile plus 5 µL of cyclohexanone weighing 0.0047 g. were added to a glass vial. Three separate injections were made in the gas chromatograph and the resultant area counts were averaged for the cyclohexanone and for the diglycidyl ether. This data was used to calculate the internal response factor, as follows:

$$\text{Internal Response Factor} = \frac{(\text{area internal standard})(\text{amount diglycidyl ethers})}{(\text{amount internal standard})(\text{area diglycidyl ethers})}$$

An aliquot (0.2500 g) of the PACE resin from Comparative Example A, acetonitrile (0.7500 g) and cyclohexanone (5 µL, 0.0042 g) were added to a glass vial and analyzed by GC. Using the data from the GC analysis plus the internal response factor, the following calculation was performed:

$$\text{Amount Diglycidyl Ethers} = \frac{(\text{amount internal standard})(\text{area diglycidyl ethers})(\text{Internal Response Factor})}{(\text{area internal standard})}$$

I.C.I. Cone and Plate Viscosity

Viscosity was determined on an I.C.I. Cone and Plate Viscometer Viscosity (model VR-4540) at 25° C. In the method, the viscometer equipped with a 0-40 poise spindle (model VR-4140) and equilibrated to 25° C. was calibrated to zero then the sample applied and held 2 min with viscosity then checked and the reading taken after 15 seconds. One or more duplicate viscosity tests were completed using a fresh aliquot of the particular product being tested. The individual measurements were averaged.

Percent Epoxide/Epoxide Equivalent Weight Analysis

A standard titration method was used to determine percent epoxide in the various epoxy resins [Jay, R. R., "Direct Titration of Epoxy Compounds and Aziridines", Analytical Chemistry, 36, 3, 667-668 (March, 1964).] In the present adaptation of this method, the carefully weighed sample (sample weight ranges from 0.17-0.18 g) was dissolved in dichloromethane (15 mL) followed by the addition of tetraethylammonium bromide solution in acetic acid (15 mL). The resultant solution treated with 3 drops of crystal violet indicator (0.1% w/v in acetic acid) was titrated with 0.1N perchloric acid in acetic acid on a Metrohm 665 Dosimat titrator (Brinkmann). Titration of a blank consisting of dichloromethane (15 mL) and tetraethylammonium bromide solution in acetic acid (15 mL) provided correction for solvent background. Percent epoxide and EEW were calculated using the following equations:

$$\% \text{ Epoxide} = \frac{[(\text{mL titrated sample}) - (\text{mL titrated blank})](0.4303)}{(\text{g sample titrated})}$$

$$EEW = \frac{4303}{\% \text{ epoxide}}$$

Differential Scanning Calorimetry (DSC)

For analysis of (1) curing of the thermosettable blend of the PACE resin or re-epoxidized PACE resin with DETA and of the (2) Tg of a cured sample a DSC 2910 Modulated DSC (TA Instruments) was employed, using a heating rate of 7° C. per min from 0° C. to 300° C. under a stream of nitrogen flowing at 35 cubic centimeters per min. Each sample was contained in an aluminum pan and loosely covered (not sealed) with an aluminum lid. The respective sample weight tested is given with the results obtained.

For analysis of curing of the thermosettable blend of the diglycidyl ether of UNOXOL™ Diol (cis-, trans-1,3- and 1,4-cyclohexanedimethanol) cured with DETA and the Tg of the thermoset thereof, the aforementioned conditions were employed, but with an end temperature of 250° C.

Comparative Example A

Three Stage Synthesis of Epoxy Resin of UNOXOL™ Diol with Postreaction Temperature Held at 40° C.

Epoxidation of UNOXOL™ Diol was performed using three stages of aqueous sodium hydroxide addition with postreaction at 40° C. followed by fractional vacuum distillation to separate the constituents of the epoxy resin:

A. Epoxidation Reaction

A 5 L, 4 neck, glass, round bottom reactor was charged with UNOXOL™ Diol (432.63 g, 3.0 moles, 6.0 hydroxyl eq), epichlorohydrin (1110.24 g, 12.0 moles, 2:1 epichlorohydrin:UNOXOL™ Diol hydroxyl eq ratio), toluene (2.5 L), and benzyltriethylammonium chloride (43.62 g, 0.1915 mole) in the indicated order. [UNOXOL™ cyclic dialcohol is a registered trademark of the Union Carbide Corporation.] The reactor was additionally equipped with a condenser (maintained at 0° C.), a thermometer, a Claisen adaptor, an overhead nitrogen inlet (1 LPM $N_2$ used), and a stirrer assembly (Teflon™ paddle, glass shaft, variable speed motor). [Teflon™ fluorocarbon resin is a trademark of E.I. duPont de Nemours.] A controller monitored the temperature registered on the thermometer in the reactor and provided heating via the heating mantle placed under the reactor as well as cooling delivered by a pair of fans positioned on the reactor exterior. Sodium hydroxide (360.0 g, 9.0 moles) dissolved in DI water (360 g) for the initial addition was added to a side arm vented addition funnel, sealed with a ground glass stopper, then attached to the reactor. Stirring commenced to give a 22.5° C. mixture followed by commencement of dropwise addition of the aqueous sodium hydroxide solution. The reaction mixture was allowed to self-heat to 40° C. during the aqueous sodium hydroxide addition time and then held at that temperature via cooling from the fans as needed. Thus, after 196 min the reaction temperature first reached 40° C. and then remained at 39-40° C. for the remainder of the aqueous sodium hydroxide addition. Addition of the aqueous sodium hydroxide required a total of 233 min. Fourteen min after completion of the aqueous sodium hydroxide addition, heating commenced to maintain the reaction at 40° C. After 16.2 hr of postreaction at 40° C., stirring ceased, and the reactor contents were allowed to settle. The organic layer was decanted from the reactor followed by addition of 1.5 L of DI water to the salt and residual toluene left behind in the reactor. After addition into a 2 L separatory funnel and settling, the toluene layer which separated from the aqueous salt solution was recovered and combined back with the decanted organic layer. The aqueous layer was discarded as waste. GC analysis after normalization to remove solvents (acetonitrile and toluene) and unreacted epichlorohydrin revealed the presence of 2.21 area % light components, 1.27 area % unreacted cis-, trans-1,3- and 1,4-cyclohexanedimethanol; 43.13 area % monoglycidyl ethers, 0.25 area % of a pair of components associated with the diglycidyl ether peaks, 50.20 area % diglycidyl ethers, and 2.94 area % oligomers that were volatile under the conditions of the GC analysis.

The organic layer was reloaded into the reactor along with fresh benzyltriethylammonium chloride (21.81 g, 0.0958 mole). Sodium hydroxide (180 g, 4.5 moles) dissolved in DI water (180 g) was added to a side arm vented addition funnel, sealed with a ground glass stopper, then attached to the reactor. Stirring commenced to give a 23.5° C. mixture followed by commencement of dropwise addition of the aqueous sodium hydroxide solution. The reaction mixture was allowed to self-heat during the aqueous sodium hydroxide addition time. Thus, after 119 min 100% of the aqueous sodium hydroxide was added causing the reaction temperature to reach a maximum of 30.5° C. Three min after completion of the aqueous sodium hydroxide addition, heating commenced to bring the reaction to 40° C. after 11 min of heating. After 15.8 hr of postreaction at 40° C., stirring ceased, and the reactor contents were allowed to settle. The organic layer was decanted from the reactor followed by addition of 1.0 L of DI water to the salt and residual toluene left behind in the reactor. After addition into a 2 L separatory funnel and settling, the toluene layer which separated from the aqueous salt solution was recovered and combined back with the decanted organic layer. The aqueous layer was discarded as waste. GC analysis after normalization to remove solvents (acetonitrile and toluene) and unreacted epichlorohydrin revealed the presence of 5.62 area % light components, no detectable unreacted cis-, trans-1,3- and 1,4-cyclohexanedimethanol; 12.63 area % monoglycidyl ethers, 0.64 area % of a pair of components associated with the diglycidyl ether peaks, 76.30 area % diglycidyl ethers, and 4.81 area % oligomers that were volatile under the conditions of the GC analysis.

The organic layer was reloaded into the reactor along with fresh benzyltriethylammonium chloride (10.91 g, 0.0479 mole). Sodium hydroxide (90 g, 2.25 moles) dissolved in DI water (90 g) was added to a side arm vented addition funnel, sealed with a ground glass stopper, then attached to the reactor. Stirring commenced to give a 23° C. mixture followed by commencement of dropwise addition of the aqueous sodium hydroxide solution. The reaction mixture was allowed to self-heat during the aqueous sodium hydroxide addition time. Thus, after 50 min 66.67% of the aqueous sodium hydroxide was added causing the reaction temperature to reach a maximum of 24.5° C. This temperature was maintained for the remainder of the aqueous sodium hydroxide addition. Addition of the aqueous sodium hydroxide required a total of 61 min. Immediately after completion of the aqueous sodium hydroxide addition, heating commenced to bring the reaction to 40° C. after 22 min of heating. After 16.7 hr of postreaction at 40° C., stirring ceased, and the reactor contents were allowed to settle. The organic layer was decanted from the reactor followed by addition of 1.0 L of DI water to the salt and residual toluene left behind in the reactor. After addition into a 2 L separatory funnel and settling, the toluene layer which separated from the aqueous salt solution was recovered and combined back with the decanted organic layer. The aqueous layer was discarded as waste. GC analysis after normalization to remove solvents (acetonitrile and toluene) and unreacted epichlorohydrin revealed the presence of 8.62 area % light components, no detectable unreacted cis-, trans-1,3- and 1,4-cyclohexanedimethanol; 9.91 area % monoglycidyl ethers, 0.46 area % of a pair of components associated with the diglycidyl ether peaks, 75.29 area % diglycidyl ethers, and 5.72 area % oligomers that were volatile under the conditions of the GC analysis.

B. Epoxy Resin Product Isolation

After removal of the aqueous layer from the reaction with the third aqueous sodium hydroxide addition, the organic layer was equally split between the pair of separatory funnels and the contents of each respective separatory funnel then washed with DI water (400 mL) by vigorously shaking. The washed product was allowed to settle for 2 hours and then the aqueous layer was removed and discarded as waste. A second wash was completed using the aforementioned method, with settling overnight (20 hr) required to fully resolve the organic and aqueous layers. The combined, hazy organic solution was filtered through a bed of anhydrous, granular sodium sulfate in a 600 mL fritted glass funnel providing a transparent filtrate.

Rotary evaporation of the filtrate using a maximum oil bath temperature of 100° C. to a final vacuum of 2.4 mm of Hg removed the bulk of the volatiles. A total of 712.20 g of light yellow colored, transparent liquid was recovered after completion of the rotary evaporation. GC analysis after normalization to remove solvent (acetonitrile) revealed the presence of 9.76 area % monoglycidyl ethers, 0.38 area % of a pair of components associated with the diglycidyl ether peaks, 82.39 area % diglycidyl ethers, and 7.47 area % oligomers that were volatile under the conditions of the GC analysis. Thus, GC analysis revealed that essentially all light boiling components, including residual epichlorohydrin, had been removed.

C. Fractional Vacuum Distillation

A portion (699.19 g) of the product from the rotary evaporation was added to a 1 L, 3 neck, glass, round bottom reactor equipped with magnetic stirring and a thermometer for monitoring the pot temperature. A one piece integral vacuum jacketed Vigreux distillation column with distillation head was used. The distillation column nominally provided 9 to 18 theoretical plates depending on the mode of operation. A second section of jacketed Vigreux distillation column was added between the one piece integral vacuum jacketed Vigreux distillation column with head and the reactor to provide an additional 9 to 18 theoretical plates. The distillation head was equipped with an overhead thermometer, air cooled condenser, a receiver and a vacuum takeoff. A vacuum pump was employed along with a liquid nitrogen trap and an in-line digital thermal conductivity vacuum gauge. Stirring commenced followed by application of full vacuum then progressively increased heating using a thermostatically controlled heating mantle. A clean receiver was used to collect each respective distillation cut. During the distillation, the initial distillation cuts were taken to sequentially remove all components boiling below the cyclohexanedimethanols, all unreacted cyclohexanedimethanols, and the bulk of the monoglycidyl ethers. The final distillation cuts sought to selectively remove diglycidyl ether, leaving the oligomeric product (279.39 g) in the distillation pot. GC analysis using a cyclohexanone internal standard revealed that the oligomers contained residual 13.91 wt % diglycidyl ether with the balance as the oligomers. After normalization to remove the peaks associated with acetonitrile solvent and the diglycidyl ether, the GC analysis demonstrated the following oligomeric components containing multiple isomers:

2.54 area % 2-propanol, 1-(oxiranylmethoxy)-3-[[3(or 4)-[(oxiranylmethoxy)methyl]cyclohexyl]methoxy]- and oxirane, 2-[[2-chloro-1-[[[3(or 4)-[(oxiranylmethoxy)methyl]cyclohexyl]methoxy]methyl]ethoxy]methyl]-

27.80 area % oxirane, 2-[[[3(or 4)-[[2,3-bis(oxiranylmethoxy)propoxy]methyl]cyclohexyl]methoxy]methyl]-

15.91 area % 2-propanol, 1,3-bis[[3(or 4)-[(oxiranylmethoxy)methyl]cyclohexyl]methoxy]-

53.74 area % oxirane, 2-[[2-[[3(or 4)-[(oxiranylmethoxy)methyl]cyclohexyl]methoxy]-1-[[[3(or 4)-[(oxiranylmethoxy)methyl]cyclohexyl]methoxy]methyl]ethoxy]methyl]-

Titration demonstrated an EEW of 193.62. I.C.I. cone and plate viscosity was 3268 cp.

Example 1

Synthesis of Re-epoxidized Polyfunctional Cycloaliphatic Oligomeric Epoxy Resin

Re-epoxidation of the polyfunctional cycloaliphatic oligomer product (Comparative Example A) was performed using two stages of aqueous sodium hydroxide addition:

A. Re-epoxidation Reaction

A 5 L, 4 neck, glass, round bottom reactor was charged with polyfunctional cycloaliphatic oligomer product (250.0 g), epichlorohydrin (277.7 g, 3.0 moles), toluene (1.0 L) and benzyltriethylammonium chloride (10.91 g, 0.0479 mole). The reactor was additionally equipped as specified above (Comparative Example A). The polyfunctional cycloaliphatic oligomer product used came from Comparative Example A, C. Fractional Vacuum Distillation. Sodium hydroxide (90.0 g, 2.25 moles) dissolved in DI water (90 g) for the initial addition was added to a side arm vented addition funnel, sealed with a ground glass stopper, then attached to the reactor. Stirring commenced to give a 23° C. mixture followed by commencement of dropwise addition of the aqueous sodium hydroxide solution. The reaction mixture was allowed to self-heat to 25° C. during the aqueous sodium hydroxide addition. Thus, after 67 min the reaction temperature first reached 25° C. and then remained at 25° C. for the remainder of the aqueous sodium hydroxide addition. Addition of the aqueous sodium hydroxide required a total of 75 min. One min after completion of the aqueous sodium hydroxide addition, heating commenced to bring the reaction to 40° C. after 22 min of heating. After 21.0 hr of postreaction at 40° C., stirring ceased, and the reactor contents were allowed to settle. The organic layer was decanted from the reactor and processed as specified above (Comparative Example A).

The organic layer was reloaded into the reactor along with fresh benzyltriethylammonium chloride (10.91 g, 0.0479 mole). Sodium hydroxide (90.0 g, 2.25 moles) dissolved in DI water (90 g) was added to a side arm vented addition funnel, sealed with a ground glass stopper, then attached to the reactor. Stirring commenced to give a 24° C. mixture followed by commencement of dropwise addition of the aqueous sodium hydroxide solution. The reaction mixture was allowed to self-heat during the aqueous sodium hydroxide addition time. Thus, after 43 min the reaction temperature first reached 25° C. and then remained at 25° C. for the remainder of the aqueous sodium hydroxide addition. Addition of the aqueous sodium hydroxide required a total of 62 min. Immediately after completion of the aqueous sodium hydroxide addition, heating commenced to bring the reaction to 40° C. after 28 min of heating. After 16.7 hr of postreaction at 40° C., stirring ceased, and the reactor contents were allowed to settle. The organic layer was decanted from the reactor and processed as specified above (Comparative Example A).

B. Epoxy Resin Product Isolation

The organic layer from the reaction was processed as specified above (Comparative Example A). Rotary evaporation of the filtrate using a maximum oil bath temperature of 100° C. to a final vacuum of 2.7 mm of Hg removed the bulk of the volatiles. A total of 251.14 g of light amber colored, transparent liquid was recovered after completion of the rotary evaporation. GC analysis using a cyclohexanone internal standard revealed that the oligomers contained residual 10.34 wt % diglycidyl ether with the balance as the oligomers. After normalization to remove the peaks associated with acetonitrile solvent and the diglycidyl ether, the GC analysis demonstrated the following oligomeric components:

0.95 area % 2-propanol, 1-(oxiranylmethoxy)-3-[[3(or 4)-[(oxiranylmethoxy)methyl]cyclohexyl]methoxy]- and oxirane, 2-[[2-chloro-1-[[[3(or 4)-[(oxiranylmethoxy)methyl]cyclohexyl]methoxy]methyl]ethoxy]methyl]-

28.56 area % oxirane, 2-[[[3(or 4)-[[2,3-bis(oxiranylmethoxy)propoxy]methyl]cyclohexyl]methoxy]methyl]-

70.49 area % oxirane, 2-[[2-[[3(or 4)-[(oxiranylmethoxy)methyl]cyclohexyl]methoxy]-1-[[[3(or 4)-[(oxiranylmethoxy)methyl]cyclohexyl]methoxy]methyl]ethoxy]methyl]-

Titration demonstrated an EEW of 181.6. I.C.I. cone and plate viscosity was 2972 cp.

Example 2

Preparation and Curing of Thermosettable Blend of Re-epoxidized Polyfunctional Oligomeric Epoxy Resin and Diethylenetriamine A portion (11.3141 g, 0.062299 epoxide equivalent) of the re-epoxidized PACE resin from Example 1 and DETA (1.289 g, 0.06247 N—H eq) were added to a glass bottle and vigorously stirred together. A portion (11.2 mg) of the homogeneous solution was removed for DSC analysis. An exotherm attributed to curing was observed with a 49.4° C. onset, 119.6° C. maximum, and a 202.94° C. endpoint accompanied by an enthalpy of 466.9 J/g.

Comparative Example B

Preparation and Curing of Thermosettable Blend of Polyfunctional Oligomeric Epoxy Resin Reactant and Diethylenetriamine A portion (11.2483 g, 0.058094 epoxide equivalent) of the PACE resin from Comparative Example A and DETA (1.200 g, 0.058156 N—H equivalent) were added to a glass bottle and vigorously stirred together. A portion (12.0 mg) of the homogeneous solution was removed for DSC analysis. An exotherm attributed to curing was observed with a 51.9° C. onset, 113.6° C. maximum, and a 212.89° C. endpoint accompanied by an enthalpy of 424.2 J/g.

Example 3

Preparation of Clear, Unfilled Casting of Thermosettable Blend of Re-epoxidized Polyfunctional Oligomeric Epoxy Resin and Diethylenetriamine and Analysis of Glass Transition Temperature The remaining portion of the re-epoxidized PACE resin and DETA blend from Example 2 was added to an aluminum dish (2.5 inch diameter by 0.5 inch deep) and cured in an oven using the following schedule: 1 hour at 70° C., 1 hour at 100° C., 1 hour at 125° C., 1 hour at 150° C. and 1 hour at 200° C. A portion (20.8 mg) of the transparent, light amber colored casting was removed for DSC analysis. A Tg of 67.2° C. was observed, with no indication of further curing or exothermic decomposition observed up to the 300° C. DSC analysis temperature. A second scanning using the aforementioned conditions again revealed a 67.0° C. Tg.

Comparative Example C

Preparation of Clear, Unfilled Casting of Thermosettable Blend of Polyfunctional Oligomeric Epoxy Resin Reactant and Diethylenetriamine and Analysis of Glass Transition Temperature The remaining portion of the PACE resin and DETA blend from Comparative Example B was added to an aluminum dish and cured using the method of Example 3. A portion (26.0 mg) of the transparent, light amber colored casting was removed for DSC analysis using a temperature range of 0° C. to 300° C. A Tg of 59.0° C. was observed, with no indication of further curing or exothermic decomposition observed up to the 300° C. DSC analysis temperature. A second scanning using the aforementioned conditions again revealed a 57.4° C. Tg.

Comparative Example D

Curing of High Purity Diglycidyl Ether of cis-, trans-1,3- and 1,4-Cyclohexanedimethanol with DETA A portion (5.0226 g, 0.03900 epoxide equivalent) of diglycidyl ether of UNOXOL™ Diol (cis-, trans-1,3- and 1,4-cyclohexanedimethanol) obtained from the fractional vacuum distillation of the epoxy resin of UNOXOL™ Diol from a three stage synthesis was added to a glass vial. G.C. analysis of the diglycidyl ether demonstrated 99.49 wt % diglycidyl ethers, 0.16 wt % monoglycidyl ethers, 0.35 wt. % of a pair of minor peaks associated with the diglycidyl ether peak and no detectable oligomers. DETA (0.81 g, 0.03926 amine hydrogen eq) was added to the glass vial then the contents were vigorously stirred together to give a homogeneous mixture. DSC analysis was completed using a 11.4 mg portion of the solution. An exothermic transition, attributable to reaction of the reactive hydrogen atoms in the curing agent with the epoxide groups, was observed with an onset temperature of 44.9° C., a maximum at 116.8° C., an enthalpy of 719.7 J/g, and an end temperature of 203.8° C. The cured product recovered from the DSC analysis was a transparent, light yellow colored, rigid solid.

Comparative Example E

Preparation of a Clear, Unfilled Casting of High Purity Diglycidyl Ether of cis-, trans-1,3- and 1,4-Cyclohexanedimethanol Cured with DETA and Analysis of Glass Transition Temperature The remaining portion of the curable mixture from Comparative Example D was added to an aluminum dish and then placed in an oven and cured using the method of Example 3. The cured product was a rigid, light amber colored, transparent solid. Portions (28.5 and 32.4 mg) of the cured product were tested by DSC analysis using the method previously given (end temperature was 250° C.). The casting obtained from curing diglycidyl ether of cis-, trans-1,3- and 1,4-cyclohexanedimethanol with DETA exhibited regions of deep channels or cracks which were first observed during the initial curing at 70° C. It is possible that the very high enthalpy on curing (Comparative Example D) may be responsible for the channels propagated through the casting. Two separate samples of the casting were randomly taken and for the DSC analyses (Tables I and II). In the DSC analyses of both Samples 1 and 2, residual exothermicity was present in the first scanning and indicated incomplete cure. Upon second scanning the residual exothermicity was no longer detected in Sample 2, but was still present Sample 1 but in a reduced amount. The large enthalpy associated with this curable mixture (Comparative Example D) may be responsible for the incomplete cure, with cure occurring so energetically that the mobility of amine groups and epoxide groups in the thermosetting matrix is restricted.

TABLE I

Glass Transition Temperature for Diglycidyl Ether of cis-, trans-1,3- and 1,4-Cyclohexanedimethanol Cured with Diethylenetriamine: Sample 1

| Tg (° C.) | Onset of Residual Exothermicity (° C.) | Peak Exotherm (° C.) | End of Residual Exothermicity (° C.) | Enthalpy (J/g) |
|---|---|---|---|---|
| 64.9 | 151.9 | 175.9 | 239.0 | 5.6 |
| 65.5 (second scanning) | 157.0 | 179.3 | 224.8 | 4.7 |

TABLE II

Glass Transition Temperature for Diglycidyl Ether of cis-, trans-1,3- and 1,4-Cyclohexanedimethanol Cured with Diethylenetriamine: Sample 2

| Tg (° C.) | Onset of Residual Exothermicity (° C.) | Peak Exotherm (° C.) | End of Residual Exothermicity (° C.) | Enthalpy (J/g) |
|---|---|---|---|---|
| 62.9 | 155.8 | 180.6 | 241.4 | 3.6 |
| 62.4 (second scanning) | none detected | | | |

Example 4

Moisture Resistance of Clear, Unfilled Casting of Thermosettable Blend of Re-epoxidized Polyfunctional Oligomeric Epoxy Resin and Diethylenetriamine A pair of coupons were cut from the clear, unfilled casting of the re-epoxidized PACE resin and DETA blend from Example 3, weighed, and each added to a polypropylene bottle containing 100 mL of DI water. One sample sealed in the polypropylene bottle was maintained at room temperature (23.5° C.) while the other was placed in an oven maintained at 55° C. The samples were removed at the respective indicated intervals, blotted with absorbent toweling, weighed and then replaced for further testing. The results are given in Table III.

Comparative Example F

Moisture Resistance of Clear, Unfilled Casting of Thermosettable Blend of Polyfunctional Oligomeric Epoxy Resin and Diethylenetriamine A pair of coupons were cut from the clear, unfilled casting of the PACE resin and DETA blend from Comparative Example C, weighed, and each added to a polypropylene bottle containing 100 mL of DI water and tested concurrently using the method of Example 4. The results are given in Table III.

TABLE III

Moisture Resistance Testing

| Sample Identification | Cumulative Time (hr) | Weight Increase in 23.5° C. DI Water (%) | Weight Increase in 55° C. DI Water (%) |
|---|---|---|---|
| PACE resin | 2.0 | 0.49 | 0.80 |
| re-epoxidized PACE resin | 2.0 | 0.36 | 0.69 |
| PACE resin | 43.5 | 1.67 | 4.98 |
| re-epoxidized PACE resin | 43.5 | 1.42 | 3.87 |
| PACE resin | 67.25 | 1.87 | 5.60 |
| re-epoxidized PACE resin | 67.25 | 1.60 | 4.39 |
| PACE resin | 93.75 | 2.10 | 6.18 |
| re-epoxidized PACE resin | 93.75 | 1.74 | 4.83 |
| PACE resin | 116.25 | 2.29 | 6.58 |
| re-epoxidized PACE resin | 116.25 | 1.88 | 5.19 |
| PACE resin | 139.75 | 2.47 | 6.96 |
| re-epoxidized PACE resin | 139.75 | 2.00 | 5.52 |
| PACE resin | 186.07 | 2.79 | 7.42 |
| re-epoxidized PACE resin | 186.07 | 2.21 | 6.03 |
| PACE resin | 210.10 | 2.86 | 7.59 |
| re-epoxidized PACE resin | 210.10 | 2.30 | 6.26 |
| PACE resin | 235.77 | 3.00 | 7.73 |
| re-epoxidized PACE resin | 235.77 | 2.39 | 6.45 |
| PACE resin | 1177.2 | 5.33 | not tested |
| re-epoxidized PACE resin | 1177.2 | 4.15 | not tested |

What is claimed is:

1. A re-epoxidized polyfunctional epoxy resin composition comprising the reaction product of:
   (I) an epoxidized polyfunctional epoxy resin oligomeric composition comprising a polyfunctional aliphatic or cycloaliphatic epoxy resin which has been isolated from an epoxy resin product formed as a result of an epoxidation process comprising the reaction of:
   (A) a material selected from the group consisting of cis-, trans-1,3- and
   1,4-cyclohexanedimethanol; cis-, trans-1,2-cyclohexanedimethanol;
   cis-, trans-1,3-cyclohexanedimethanol; cis-, trans-1,4-cyclohexanedimethanol; 4-methyl-1,2-cyclohexanedimethanol;
   4-methyl-1, 1-cyclohexanedimethanol; 1,1-cyclohexanedimethanol; a cyclohexenedimethanol including 3-cyclohexene-1,1-dimethanol;
   3-cyclohexene-1,1-dimethanol, 6-methyl-; 4,6-dimethyl-3-cyclohexene-1,1-dimethanol; cyclohex-2-ene-1,1-dimethanol; 1,1-cyclohexanediethanol;
   1,4-bis(2-hydroxyethoxy)cyclohexane; 1,4-cyclohexanediethanol;
   and 1,4-bis(2-hydroxyethyloxy)cyclohex-2-ene;
       (B) an epihalohydrin,
       (C) a basic-acting substance,
       (D) a non-Lewis acid catalyst; and
       (E) optionally, one or more solvents;
   (II) an epihalohydrin;
   (III) a basic acting substance;
   (IV) a non-Lewis acid catalyst; and
   (V) optionally, one of more solvents.

2. A process for preparing a re-epoxidized polyfunctional epoxy resin composition comprising reacting:
   (I) an epoxidized polyfunctional epoxy resin oligomeric composition comprising a polyfunctional aliphatic or cycloaliphatic epoxy resin which has been isolated from an epoxy resin product formed as a result of an epoxidation process comprising the reaction of:
   (A) a material selected from the group consisting of cis-, trans-1,3- and
   1,4-cyclohexanedimethanol; cis-, trans-1,2-cyclohexanedimethanol;
   cis-, trans-1,3-cyclohexanedimethanol; cis-, trans-1,4-cyclohexanedimethanol; 4-methyl-1,2-cyclohexanedimethanol;
   4-methyl-1,1-cyclohexanedimethanol; 1,1-cyclohexanedimethanol; a cyclohexenedimethanol including 3-cyclohexene-1,1-dimethanol;
   3-cyclohexene-1,1-dimethanol, 6-methyl-; 4,6-dimethyl-3-cyclohexene-1,1-dimethanol; cyclohex-2-ene-1,1-dimethanol; 1,1-cyclohexanediethanol;
   1,4-bis(2-hydroxyethoxy)cyclohexane; 1,4-cyclohexanediethanol;
   and 1,4-bis(2-hydroxyethyloxy)cyclohex-2-ene;
       (B) an epihalohydrin,
       (C) a basic-acting substance,
       (D) a non-Lewis acid catalyst; and
       (E) optionally, one or more solvents;
   (II) an epihalohydrin;
   (III) a basic acting substance;
   (IV) a non-Lewis acid catalyst; and;
   (V) optionally, one or more solvents.

* * * * *